(12) United States Patent
Powell et al.

(10) Patent No.: US 7,661,956 B2
(45) Date of Patent: Feb. 16, 2010

(54) METHODS FOR MANUFACTURING DENTAL IMPLANT COMPONENTS

(75) Inventors: Theodore M. Powell, Jupiter, FL (US); Bruce Berckmans, III, Palm Beach Gardens, FL (US); Zachary B. Suttin, Palm Beach Gardens, FL (US); Dan P. Rogers, North Palm Beach, FL (US); T. Tait Robb, Stewart, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 515 days.

(21) Appl. No.: 11/585,705

(22) Filed: Oct. 24, 2006

(65) Prior Publication Data

US 2007/0092854 A1    Apr. 26, 2007

Related U.S. Application Data

(60) Provisional application No. 60/729,506, filed on Oct. 24, 2005.

(51) Int. Cl.
*A61C 13/12*    (2006.01)
*A61C 11/00*    (2006.01)
*A61C 9/00*    (2006.01)

(52) U.S. Cl. .................. 433/172; 433/213; 433/214

(58) Field of Classification Search ......... 433/172–176, 433/213–214; 700/245–264; 901/2
See application file for complete search history.

(56) References Cited

U.S. PATENT DOCUMENTS

| 3,958,471 | A | 5/1976 | Muller |
| 4,011,602 | A | 3/1977 | Rybicki et al. |
| 4,086,701 | A | 5/1978 | Kawahara et al. |
| 4,177,562 | A | 12/1979 | Miller et al. |
| 4,306,862 | A | 12/1981 | Knox |
| 4,341,312 | A | 7/1982 | Scholer |
| 4,547,157 | A | 10/1985 | Driskell |

(Continued)

FOREIGN PATENT DOCUMENTS

WO    WO 2003/024352 A1    3/2003

OTHER PUBLICATIONS

International Search Report—Dated Sep. 25, 2007 (2 pgs).

*Primary Examiner*—Cris L Rodriguez
*Assistant Examiner*—Matthew M Nelson
(74) *Attorney, Agent, or Firm*—Nixon Peabody LLP

(57) ABSTRACT

A method of manufacturing a rapid prototype overmold for locating a dental implant analog in a modified stone model for use in creating a tooth prosthesis is provided. An impression of a mouth having a first installation site that has a dental implant and a gingival healing abutment with at least one informational marker installed is taken. A stone model based on the impression is prepared. The model is scanned. A three-dimensional computer model of the installation site on a CAD program using data from the scan is created. The at least one informational marker is determined to gather information about the location of the dental implant. Abutment dimensional information based on the three-dimensional image and the at least one informational marker is developed. Overmold rapid prototype dimensional information based on the three-dimensional image is developed. The overmold rapid prototype adapted to fit over the modified stone model is fabricated.

9 Claims, 23 Drawing Sheets

U.S. PATENT DOCUMENTS

| | | |
|---|---|---|
| 4,624,673 A | 11/1986 | Meyer |
| 4,713,004 A | 12/1987 | Linkow et al. |
| 4,758,161 A | 7/1988 | Niznick |
| 4,767,331 A | 8/1988 | Hoe |
| 4,772,204 A | 9/1988 | Soderberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,988,297 A | 1/1991 | Lazzara et al. |
| 4,988,298 A | 1/1991 | Lazzara et al. |
| 5,000,685 A | 3/1991 | Brajnovic |
| 5,006,069 A | 4/1991 | Lazzara et al. |
| 5,015,186 A | 5/1991 | Detsch |
| 5,030,096 A | 7/1991 | Hurson et al. |
| 5,035,619 A | 7/1991 | Daftary |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,135,395 A | 8/1992 | Marlin |
| 5,145,371 A | 9/1992 | Jörnéus |
| 5,145,372 A | 9/1992 | Daftary et al. |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,246,370 A | 9/1993 | Coatoam |
| 5,281,140 A | 1/1994 | Niznick |
| 5,286,195 A | 2/1994 | Clostermann |
| 5,292,252 A | 3/1994 | Nickerson et al. |
| 5,297,963 A | 3/1994 | Dafatry |
| 5,312,254 A | 5/1994 | Rosenlicht |
| 5,316,476 A | 5/1994 | Krauser |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,344,457 A | 9/1994 | Pilliar et al. |
| 5,362,234 A | 11/1994 | Salazar et al. |
| 5,362,235 A | 11/1994 | Daftary |
| 5,368,483 A | 11/1994 | Sutter et al. |
| 5,370,692 A | 12/1994 | Fink |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,564,921 A | 10/1996 | Marlin |
| 5,564,924 A | 10/1996 | Kwan |
| 5,651,675 A | 7/1997 | Singer |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,741,215 A | 4/1998 | D'Urso |
| 5,759,036 A | 6/1998 | Hinds |
| 5,768,134 A | 6/1998 | Swaelens |
| 5,813,858 A | 9/1998 | Singer |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,938,443 A | 8/1999 | Lazzara et al. |
| 5,989,029 A | 11/1999 | Osorlo |
| 6,120,293 A | 9/2000 | Lazzara et al. |
| 6,129,548 A | 10/2000 | Lazzara et al. |
| 6,135,773 A | 10/2000 | Lazzara |
| 6,210,162 B1 | 4/2001 | Chishti |
| 6,217,334 B1 | 4/2001 | Hultgren |
| 6,322,728 B1 | 11/2001 | Brodkin |
| 6,540,784 B2 | 4/2003 | Barlow |
| 6,619,958 B2 | 9/2003 | Beaty et al. |
| 6,629,840 B2 | 10/2003 | Chishti |
| 6,691,764 B2 | 2/2004 | Embert |
| 6,772,026 B2 | 8/2004 | Bradbury |
| 6,808,659 B2 | 10/2004 | Schulman |
| 6,829,498 B2 | 12/2004 | Kipke et al. |
| 2002/0028418 A1 | 3/2002 | Farag et al. |
| 2002/0167100 A1 | 11/2002 | Moszner |
| 2003/0222366 A1 | 12/2003 | Stangel |
| 2004/0220691 A1 | 11/2004 | Hofmeister et al. |
| 2005/0056350 A1 | 3/2005 | Dolabdjian et al. |

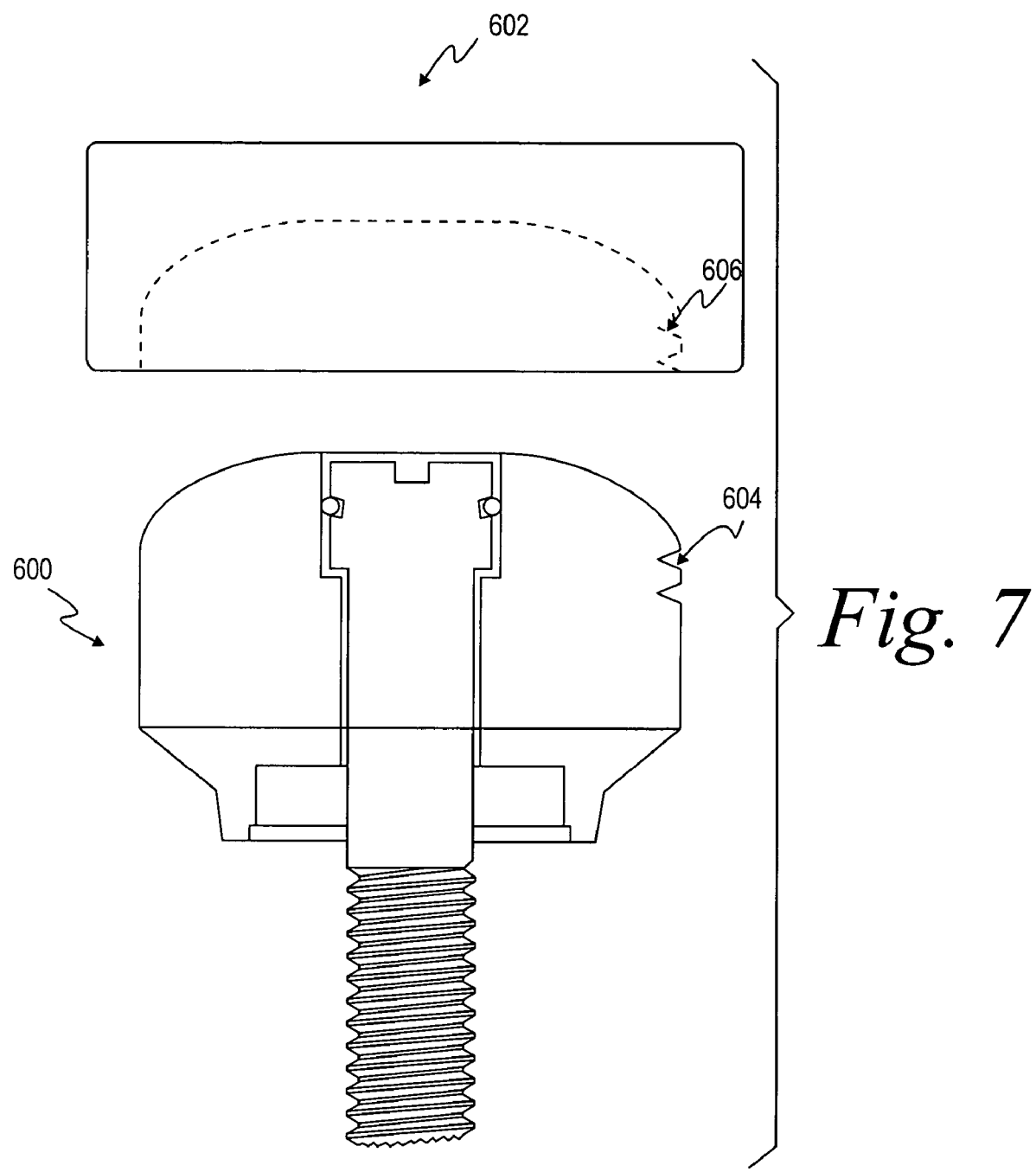

METHODS FOR MANUFACTURING DENTAL IMPLANT COMPONENTS

RELATED APPLICATIONS

This application claims the benefit of U.S. Provisional Patent Application No. 60/729,506 filed on Oct. 24, 2005 and entitled "Methods for Manufacturing Dental Implant Components" and this provisional application is herby incorporated by reference in its entirety.

FIELD OF INVENTION

The present invention relates generally to dental implant systems. More particularly, the present invention relates to restoration components for dental implant systems and a computer model for developing an implant analog placement tool to eliminate the need for a surgical index.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is made. The impression coping may be a "pick-up" type impression coping or a "transfer" type impression coping, both known in the art. After these processes, a dental laboratory creates a prosthesis to be permanently secured to the dental implant from the impression that was made.

In addition to the method that uses the impression material and mold to manually develop a prosthesis, systems exist that utilize scanning technology to assist in generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and surrounding area is scanned. Third, a dentist or technician can scan the stone model of the dental region that was formed from the impression material and mold to produce the permanent components.

Three basic scanning techniques exist, laser scanning, photographic imaging and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer aided design ("CAD") package.

The utilization of a CAD program, as disclosed in U.S. Pat. No. 5,338,198, (Wu), whose disclosure is incorporated by reference herein, is one method of scanning a dental region to create a three dimensional model. Preferably, after the impression is made of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known location in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known means.

Photographic imaging can also used to scan impression material, a stone model or to scan directly in the mouth. For example, one system takes photographs at multiple angles in one exposure to scan a dental region, create a model and manufacture a prosthetic tooth. As disclosed in U.S. Pat. No. 5,851,115, (Carlsson), whose disclosure is incorporated by reference herein, this process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position and other details of the model, the ultimate step is the transmission of the data to a computer for manufacturing.

A third scanning measure uses mechanical sensing. A mechanical contour sensing device, as disclosed in U.S. Pat. No. 5,652,709 (Andersson), whose disclosure is incorporated by reference herein, is another method used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer then compresses the data for storage and/or transmission to the milling equipment.

When the stone model of the patient's mouth is created for use in the scanning process, or in other prior techniques, a second stone model of the patient's mouth is also typically used to develop a final prosthesis for use in the patient. The prosthesis is typically developed on the second stone model. A surgical index is used to position the implant analog within the second stone model so that the dental laboratory may know the exact position of the implant when making the prosthesis. The surgical index is typically a mold of the patient's teeth directly adjacent to the implant site that relies upon the position of the adjacent teeth to dictate the location and orientation of the implant analog within the stone model. Unfortunately, the surgical index is an additional step in the process for the clinician that requires additional components. A need exists for a device and method of placing the implant analog within the stone model without using a conventional surgical index.

SUMMARY OF THE INVENTION

According to one process of the present invention a method of manufacturing a rapid prototype overmold for locating a dental implant analog in a modified stone model for use in creating a tooth prosthesis is provided. The method takes an impression of a mouth that includes a first installation site that has a dental implant installed in the first installation site and a gingival healing abutment that has at least one informational marker. The gingival healing abutment is attached to the dental implant. The process prepares a stone model based on the impression. The stone model includes teeth models and model markers indicative of the at least one informational marker. The method scans the model. The scan of the model generates scan data. The method transfers the scan data to a CAD program. The process creates a three-dimensional computer model of the installation site on the CAD program using the scan data. The method determines the at least one informational marker to gather information about the location of the dental implant. The process develops abutment dimensional information based on the three-dimensional image and the at least one informational marker. The process develops overmold rapid prototype dimensional information based on the three-dimensional image and the abutment dimensional information. The process transfers the overmold rapid prototype dimensional information to a rapid prototyping machine. The method fabricates the overmold rapid prototype adapted to fit over the modified stone model. The overmold rapid prototype is adapted to receive a custom abutment developed from the abutment dimensional information. The custom abutment has an implant analog attached. The overmold rapid prototype is further adapted to position the custom abutment and the implant analog within the modified stone model by registering the overmold rapid prototype on at least one tooth model of the modified stone model.

According to another process of the present invention, a method of manufacturing a rapid prototype overmold for locating a dental implant analog in a modified stone model for use in creating a tooth prosthesis comprising the following acts. The method prepares a stone model of a mouth that has a first installation site that has a dental implant installed in the first installation site and a gingival healing abutment that has at least one informational marker. The gingival healing abutment is attached to the dental implant. The stone model includes teeth models and model markers indicative of the at least one informational marker. The process scans the model. The scan of the model generates scan data. The scan data is transferred to a CAD program. The process creates a three-dimensional computer model of the installation site on the CAD program using the scan data. The method determines the at least one informational marker to gather information for manufacturing a patient specific custom abutment. Custom abutment dimensional information is developed on the CAD program. The process generates overmold rapid prototype dimensional information based on the three-dimensional image and the custom abutment dimensional information. The overmold rapid prototype is adapted to fit over at least a portion of a modified stone model to position an implant analog within the modifed stone model. The process provides the overmold rapid prototype dimensional information to a rapid prototyping machine. The method fabricates the overmold rapid prototype.

According to a further process of the present invention a method of manufacturing a rapid prototype overmold for locating a dental implant analog in a modified stone model for use in creating a tooth prosthesis comprises the following acts. The process installs a dental implant into a first installation site in bone having overlying gingiva in a mouth. The method attaches an attachment member to the dental implant. The attachment member having at least one informational marker for identifying physical characteristics of the attachment member. The process takes an impression of the mouth including the first installation site. A stone model based on the impression is prepared. The stone model includes teeth models and model markers indicative of the at least one informational marker. The method scans the model. The scan generates scan data. The method transfers the scan data to a graphical imaging software program. The process creates a three-dimensional image of the installation site. The process determines the model markers to gather information for manufacturing the custom-abutment. The method develops custom-abutment dimensional information based on the three-dimensional image and the information gathered from the at least one informational marker. The process transfers the custom-abutment dimensional information to a milling machine. The method fabricates the custom-abutment on the milling machine utilizing the custom-abutment dimensional information. The method determines the at least one informational marker to gather information for manufacturing a rapid prototype of an overmold for the stone model, including information regarding the location of the dental implant. The process develops rapid prototype dimensional information for the overmold based on the three-dimensional image and the custom-abutment dimensional information. The rapid prototype dimensional information for the overmold transfers to a rapid prototyping machine. The rapid prototyping machine fabricates the rapid prototype of the overmold for the modified stone model on using the rapid prototype dimensional information for the overmold. The process modifies the stone model by removing the model markers from the stone model. The custom abutment and a dental implant analog attach to the rapid prototype of the overmold for the stone model. The process places the rapid prototype of the overmold for the stone model onto the modified stone model, such that the overmold positions the custom-abutment as shown in the three-dimensional image. The method secures the implant analog to the modified stone model using a securing material. The process removes the rapid prototype of the overmold from the modified stone model after securing the implant analog. The process produces a tooth-like prosthetic adapted to mate with the custom abutment.

According to yet another process of the present invention, a method of manufacturing a rapid prototype overmold for locating a dental implant analog in a modified stone model for use in creating a tooth prosthesis is provided. The method installs a dental implant into a first installation site in bone having overlying gingiva in a mouth. An attachment member attaches to the dental implant. The attachment member has at least one informational marker for identifying physical characteristics of the attachment member. The process takes an impression of the mouth including the first installation site. The method prepares a stone model based on the impression. The stone model includes teeth models and model markers indicative of the at least one informational marker. The process scans the model. The scan of the model generates scan data. The scan data transfers to a graphical imaging software program. The process creates a three-dimensional image of the installation site. The method determines the model markers to gather information for manufacturing the custom-abutment. Custom-abutment dimensional information develops based on the three-dimensional image and the information gathered from the at least one informational marker. The custom-abutment dimensional information transfers to a milling machine. The milling machine fabricates the custom-abutment utilizing the custom-abutment dimensional information. The process determines the at least one informational marker to gather information for manufacturing a rapid prototype of an overmold for the stone model, including information regarding the location of the dental implant. The method develops rapid prototype dimensional information for the overmold based on the three-dimensional image and the custom-abutment dimensional information. The rapid prototype dimensional information for the overmold transfers to a rapid prototyping machine. The process fabricates the rapid prototype of the overmold for the modified stone model on the rapid prototyping machine using the rapid prototype dimensional information for the overmold. The stone model is modified by removing the model markers from the stone model. The custom abutment and a dental implant analog are attached to the rapid prototype of the overmold for the stone model. The method places the rapid prototype of the overmold for the stone model onto the modified stone model, such that the overmold positions the custom-abutment as shown in the three-dimensional image. The implant analog is secured to the modified stone model using a securing material. The rapid prototype of the overmold is removed from the modified stone model after securing the implant analog. A tooth-like prosthesis adapted to mate with the custom abutment is produced.

According to yet another process of the present invention, A method of positioning an implant analog in a modified stone model of a patient's dentition for use in creating a patient specific prosthesis is provided. A stone model of a patient's dentition including teeth models and model markers indicative of the at least one informational marker is prepared. The stone model is scanned. The scanning of the model generates scan data. The scan data is transferred to a CAD program. The process creates a three-dimensional model of the installation site on the CAD program using the scan data. The at least one informational marker is determined to gather information for manufacturing an abutment. Abutment dimensional information is developed based on the three-dimensional image and the at least one informational marker. The process attaches an implant analog to the abutment on the CAD program. Implant analog positional information is developed on the CAD program. The implant analog positional information is transferred to a robot manipulator. The method modifies the stone model by removing the model markers. The implant analogs are placed on the modified stone model using the robot manipulator and the implant analog positional information.

According to one embodiment of the present invention A dental component comprises a rapid prototype overmold adapted to be positioned over dentition of a modified physical model of a patient's mouth. The rapid prototype overmold is created from a CAD image of the patient's mouth. The rapid prototype overmold is adapted to receive a custom abutment and an implant analog. The custom abutment is designed based on the CAD image. The rapid prototype overmold is further adapted to position the abutment and the implant analog at a location in the modified physical model substantially corresponding to the CAD image by registering the rapid prototype overmold on at least one tooth model of the modified physical model.

According to still yet another process of the present invention, a method of manufacturing an overmold for locating a dental implant analog in a modified stone model used in creating a tooth prosthesis is provided. On a CAD program, a three-dimensional computer model of at least two teeth in a patient's mouth and an implant installation site near the two teeth is created. The location and orientation of a dental implant within the implant installation site is determined. The method develops, on a CAD program, a three-dimensional image of an abutment for mating with the dental implant. The process develops, on a CAD program, a three-dimensional image of an overmold that is based on the three-dimensional abutment image and the at least two teeth model. The three-dimensional overmold image dimensionally interacts with the at least two teeth model and the three-dimensional abutment image. The overmold from the three-dimensional overmold image is fabricated. The overmold has teeth-receiving regions for receiving a model of the least two teeth on an overall model of the patient's mouth. The overmold has an abutment-receiving region for receiving the abutment to be mated with an implant analog used in said overall model of the patient's mouth.

According to still yet a further process of the present invention, a method of positioning an implant analog in a modified stone model of a patient's dentition for use in creating a patient specific prosthesis is provided. The process creates, on a CAD program, a three-dimensional computer model of at least two teeth in a patient's mouth and an implant installation site near the two teeth. The location and orientation of a dental implant within the implant installation site is determined. The method develops, on a CAD program, a three-dimensional image of an abutment for mating with the dental implant. Implant analog positional information is generated on the CAD program. An implant analog is attached to the abutment on the CAD program. The implant analog positional information is transferred to a robot manipulator. The process modifies stone model by removing the model markers. The implant analogs are placed on the modified stone model using the robot manipulator and the implant analog positional information.

BRIEF DESCRIPTION OF THE DRAWINGS

FIG. 1b is a longitudinal cross-sectional view of the healing abutment shown in FIG. 1a;

FIG. 2b is a longitudinal cross-sectional view of the healing abutment shown in FIG. 2a;

FIG. 3b is a longitudinal cross-sectional view of the healing abutment shown in FIG. 3a.

FIG. 4b is a longitudinal cross-sectional view of the healing abutment shown in FIG. 4a;

FIG. 5b is a longitudinal cross-sectional view of the healing abutment shown in FIG. 5a;

FIG. 6b is a longitudinal cross-sectional view of the healing abutment shown in FIG. 6a;

FIG. 7 is an exploded view of another embodiment of the present application;

Figure 1A:
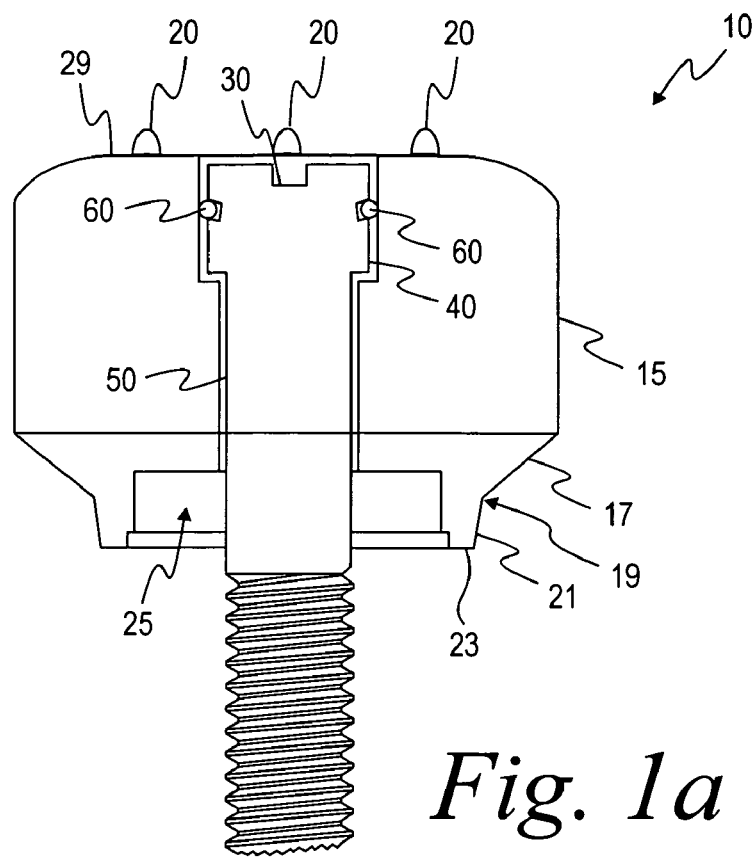
FIG. 1a is a top view of a healing abutment.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1B:
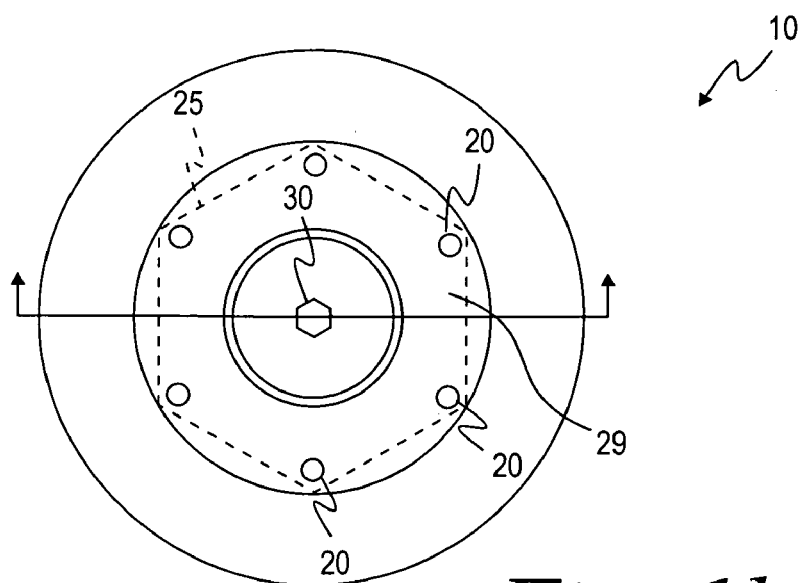

As shown in FIG. 1a and 1b, the healing abutment 10 of one embodiment of the present invention has a main body 15 with a generally circular cross-sectional shape, a first tapered section 17, a boundary 19, a second tapered section 21, an end surface 23, a hex socket 25 and dimensions that are generally suitable for replicating the emergence profile of a natural tooth. The first tapered section 17 extends downwardly from the main body 15 of the abutment 10 having a diameter at a boundary 19 that is generally larger than the implant (not shown). The boundary 19 separates the first tapered section 17 from the second tapered section 21 that terminates in the end surface 23. The second tapered section 21 is at an angle with the central axis of the implant that is generally in the range from about 5 degrees to about 15 degrees, with 10 degrees being preferable. Alternatively, the second tapered section 21 may be omitted such that the first tapered section 17 tapers directly to the diameter of the end surface 23 of the implant. In a further embodiment, the first tapered section 17 may merge smoothly into the second tapered section 21, without the distinct boundary 19 separating the two tapered sections 17 and 21. The hexagonal orientation socket or hex 25 is for mating with a hexagonal boss on the implant. The end surface 23 has generally the same diameter as the seating surface of the implant.

FIG. 1b discloses the top view of the same healing abutment 10 shown in FIG. 1a. As shown in FIGS. 1a and 1b, the healing abutment 10 has positive information markers 20 protruding from a top surface 29 of the healing abutment 10. Each of the six positive information markers 20 is disposed such that it aligns with the six corners of the underlying hex 25. It is also contemplated in accordance with the present invention that the six information markers 20 may also correspond to the height of the healing abutment. For example, two information markers might correspond to a 2 mm tall healing abutment and four information markers might correspond to a healing abutment that is 4 mm tall. In these embodiments, the two or four information markers would still be at the corners of the underlying hex 25 so that the relative position of the hex is known.

Figure 1C:
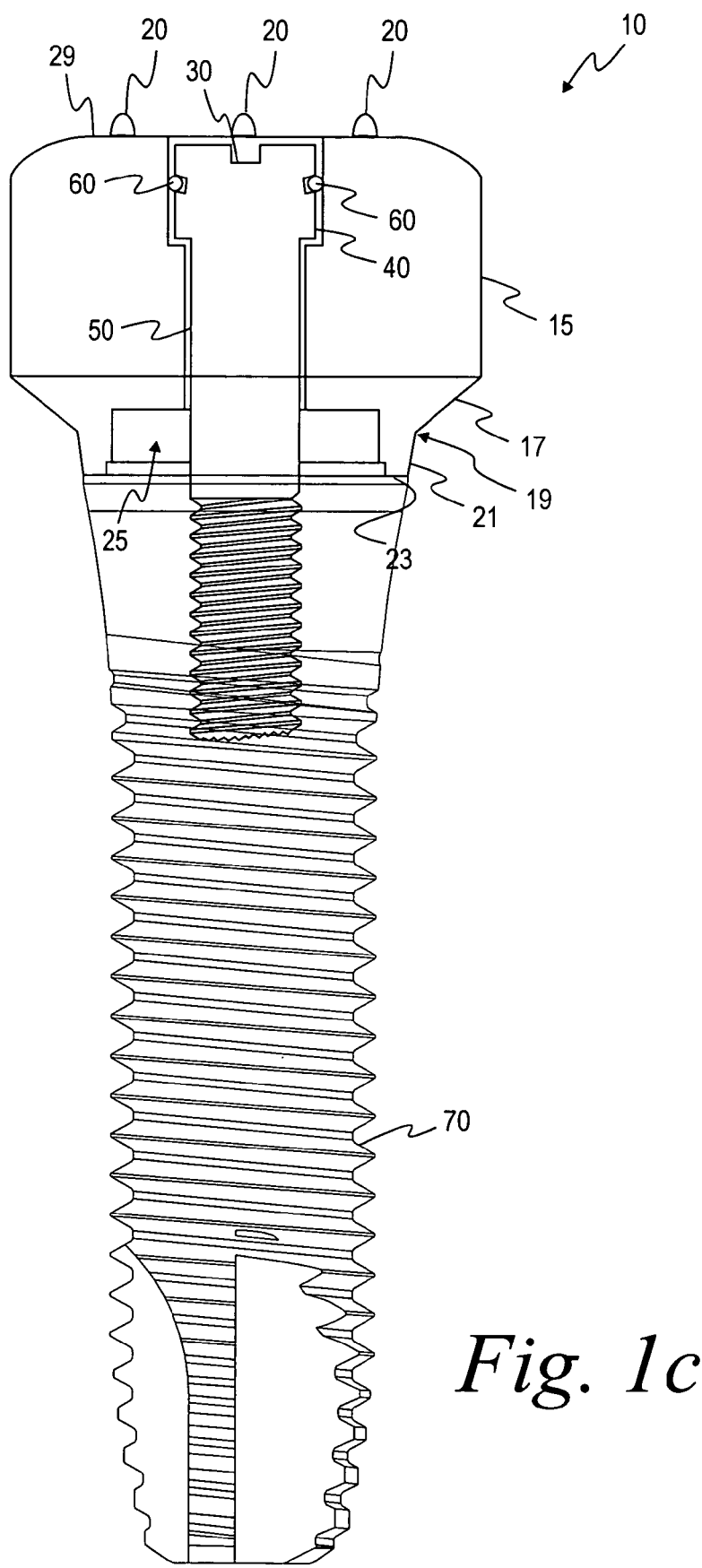
FIG. 1c is the healing abutment shown in FIG. 1b attached to an implant.

A socket 30 on the exposed surface of a head portion 40 of an attaching bolt 50 is shaped to accept a wrench (not shown) for turning the attaching bolt 50 into the threaded bore of an implant 70, as shown in FIG. 1c. It is contemplated in accordance with the present invention that each of the healing abutments described herein and shown in the figures can be secured to an implant by means of an attaching bolt, as is known in the art. An 0-ring 60 carried on the head portion 40 of the attaching bolt 50 fills an annular gap left between the head and the entrance section near the outermost (widest) opening in the entrance section.

Figure 2A:
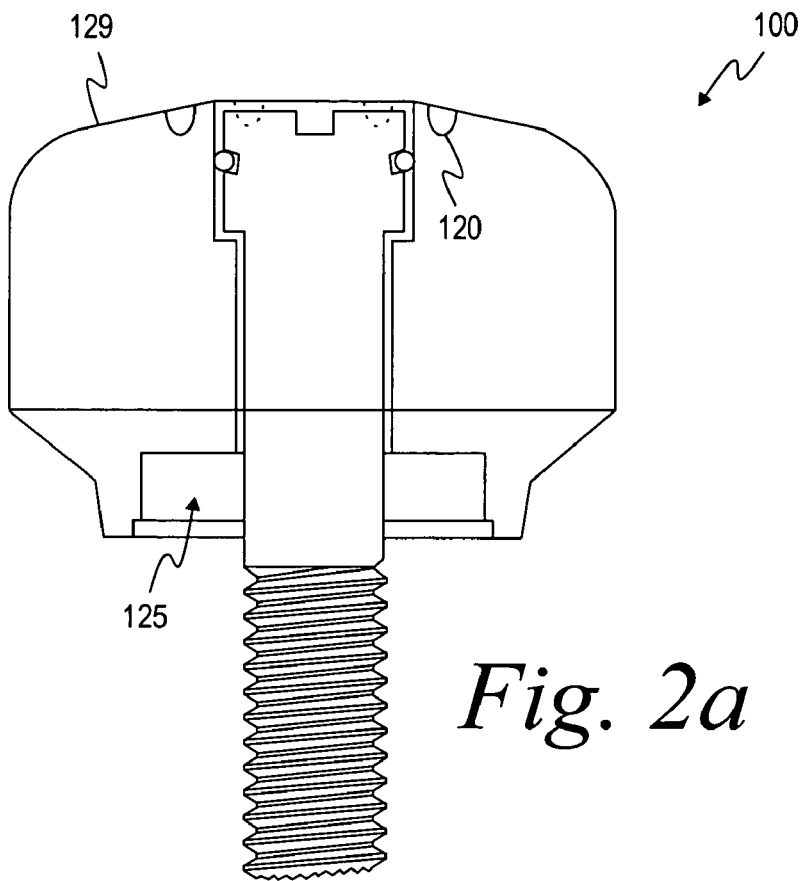
FIG. 2a is a top view of another embodiment of a healing abutment.
Figure 2B:
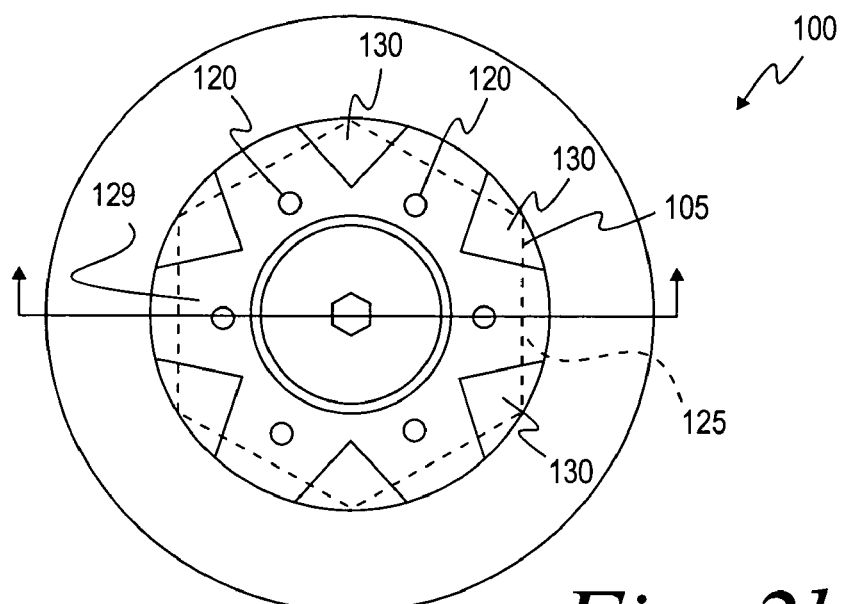

A healing abutment 100 of FIG. 2a comprises many of the same features as the healing abutment 10 shown in FIG. 1a. Dashed lines 125 in FIG. 2b correspond to the underlying hex 125 of the healing abutment 100 in FIG. 2a. A top surface 129 includes negative information markers (recesses) 120 that are displayed in FIG. 2a as dimples extending below the top surface 129 of the healing abutment 100. The top surface 129 of the healing abutment 100 also possesses six notches 130 that are machined into the corners. The top surface 129 is generally flat and merges into a rounded shape at the periphery of the healing abutment 100.

The notches 130 are used, for example, to determine the identification of the underlying implant hex position 125 or the height of the healing abutment or the diameter of the healing abutment. This embodiment is not limited to comprising six notches in the top surface 129 of the healing abutment 100. It is also contemplated that one embodiment of the present invention may possess four notches or even two notches for indicative purposes. Furthermore, it is contemplated that the information marker and notch approach could be combined or modified to provide information regarding the underlying implant seating surface diameter and implant hex angulation.

Figure 3A:
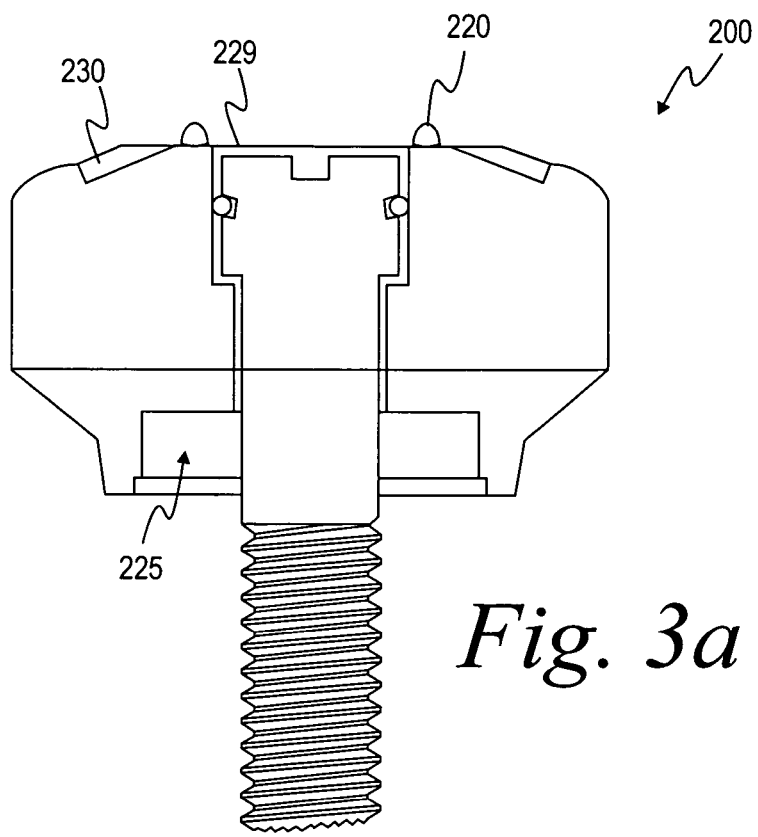
FIG. 3a is a top view of yet another embodiment of a healing abutment.
Figure 3B:
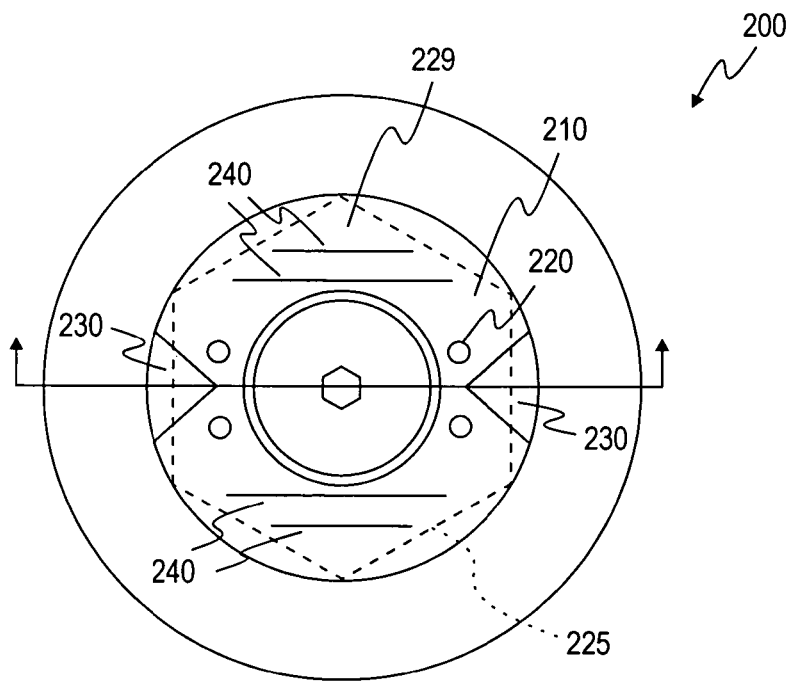

In another embodiment of the present invention, a healing abutment 200 shown in FIGS. 3a and 3b displays four positive information markers 220 shown to, for example, indicate a 4 mm tall healing abutment 200. It is contemplated that the number of information markers 220 could decrease or increase depending on the height of the healing abutment 200 or another variable that the information markers have been designated to correspond. The positive information markers 220 also define a corresponding one of the six flat surfaces of an underlying hex 225. Furthermore, dashed lines 225 in FIG. 3b correspond directly to the underlying hex 225.

Figure 4A:
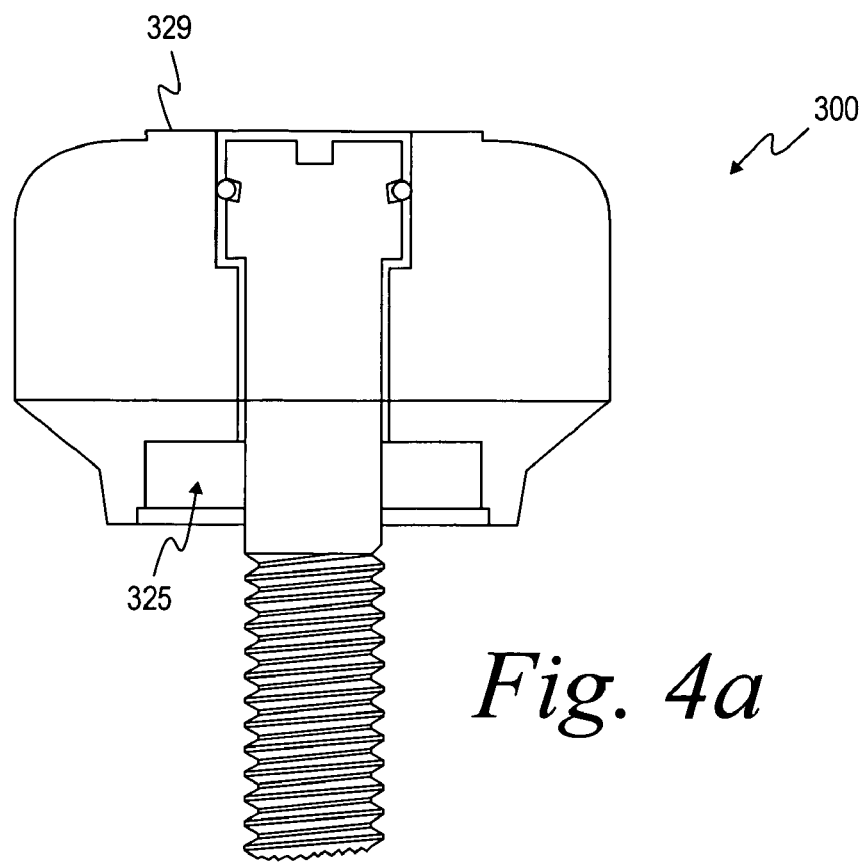
FIG. 4a is a top view of a further embodiment of the healing abutment.
Figure 4B:
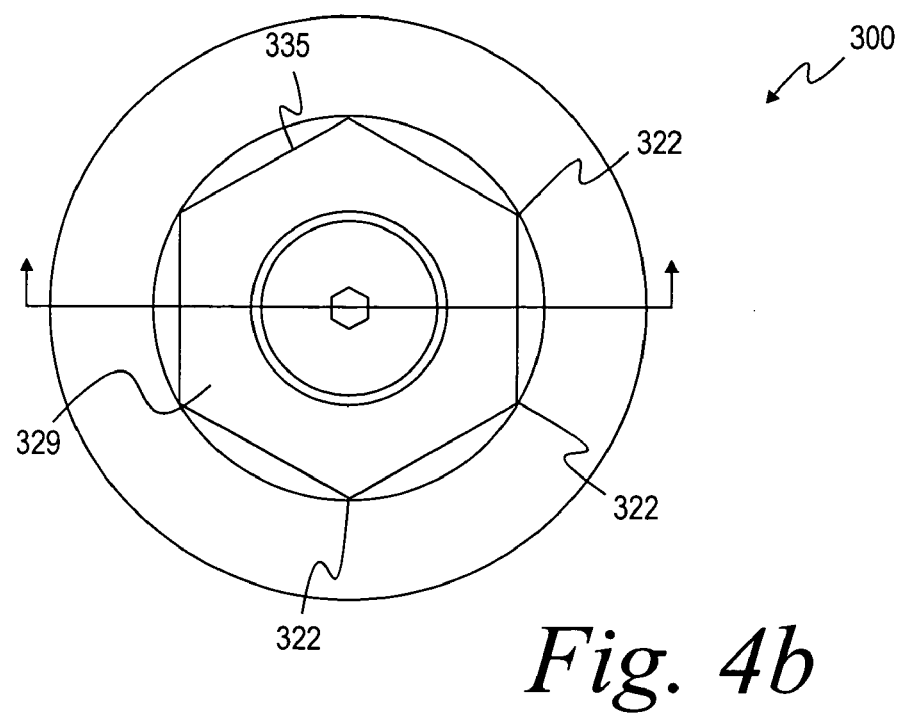

Two notches 230 have also been etched or machined onto a top surface 229 of the healing abutment of FIG. 3b. These notches may indicate the diameter of the implant's seating surface. Lines 240 are scribed on the top surface 229 of the healing abutment 200. The lines 240 are used to provide positioning or other information to the dentist or laboratory. Here, the lines 240 indicate the diameter of the healing abutment (e.g., 4 mm). In summary, the number of the positive information markers 220 indicates the height of the healing abutment 200. The position of the positive information markers 220 indicates the orientation of the hex 225 that is the orientation of the hexagonal boss on the implant. The notches 230 indicate the diameter of the seating surface of the implant. The lines 240 indicate the diameter of the healing abutment 200. generally In yet another embodiment of the present invention, a top surface 329 of the healing abutment 300 of FIGS. 4a and 4b comprises an etched or machined hex 335. Corners 322 of the etched hex 335 correspond directly to the position of the corners of an underlying hex 325 shown in FIG. 4a. It is contemplated in accordance with one embodiment of the present invention that further information markers may be added to the healing abutment for the dentist or laboratory to ascertain different heights or diameters.

Figure 5A:
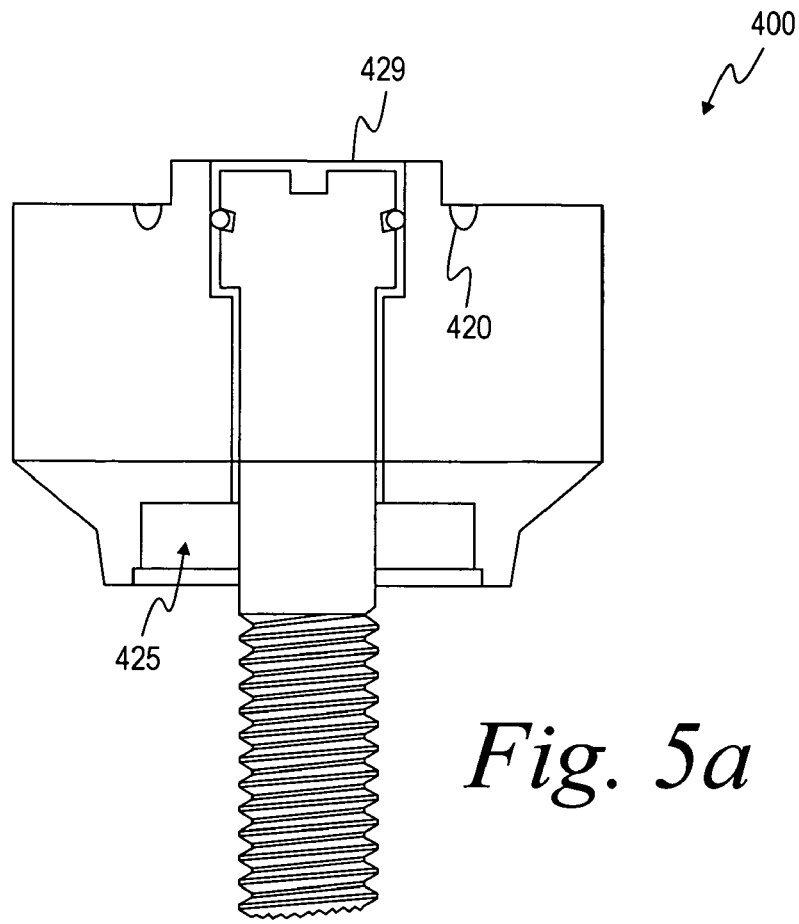
FIG. 5a is a top view of another embodiment of a healing abutment.
Figure 5B:
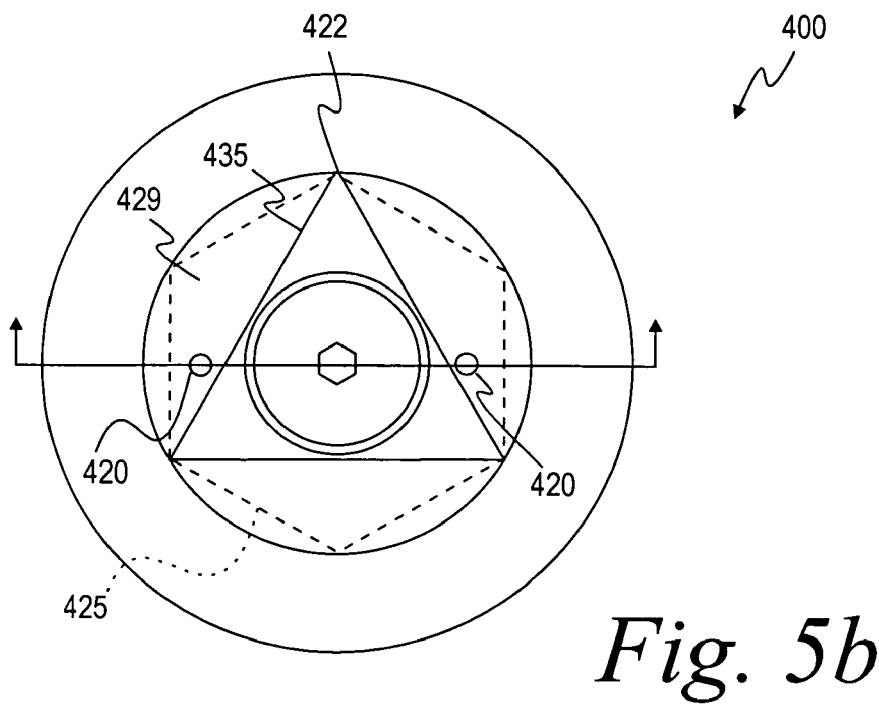

A top surface 429 of a healing abutment 400 shown in FIGS. 5a and 5b contains an etched or machined triangle 435. Dashed lines 425 in FIG. 5b indicate the location of an underlying hex 425. Corners 422 of the etched triangle 435 correspond to three of the six corners of the underlying hex 425. Furthermore, two negative information markers 420 are shown in FIG. 5b. As above, it is contemplated in accordance with the present invention that fewer than six information markers may exist to account for differing heights or diameters of the healing abutments.

Figure 6A:
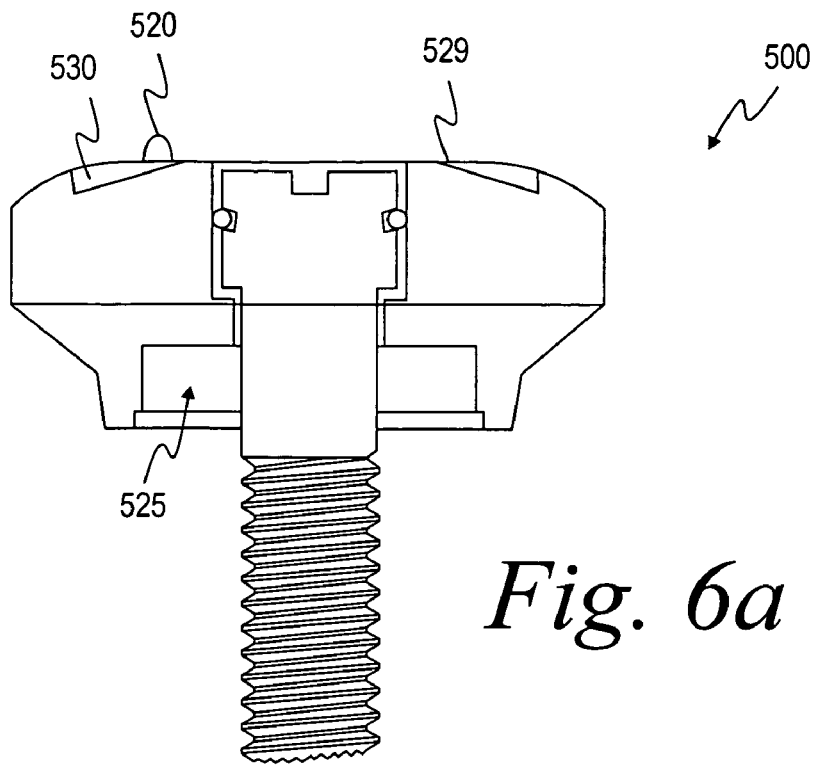
FIG. 6a is a top view of another embodiment of a healing abutment.
Figure 6B:
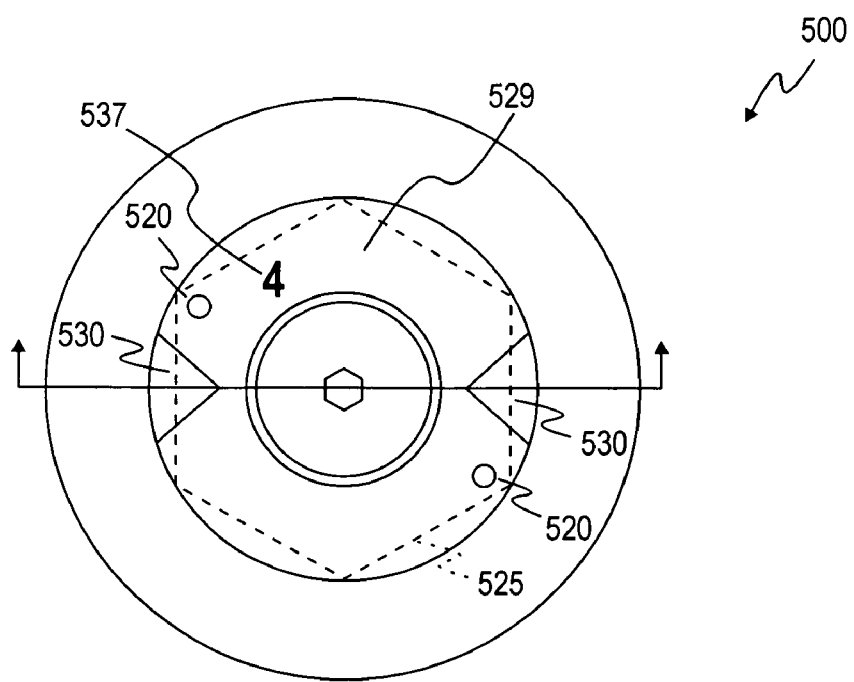

Another embodiment of the present invention is shown in FIGS. 6a and 6b. The healing abutment 500 displayed in FIGS. 6a and 6b is a shorter version of the healing abutment 10 shown in FIGS. 1a and 1b. Two positive information markers 520 are shown in FIG. 6b to identify the height of the healing abutment 500. Dashed lines 525 of the healing abutment 500 correspond with the location and orientation of the underlying hex 525. Two notches 530 are also shown in a top surface 529 of this embodiment of the present invention to show the orientation of two of the underlying flats of the underlying hex 525. A numeral "4" at 537 is located on the top surface 529 of the healing abutment 500 to indicate, for example, the diameter of the healing abutment 500. As shown, the numeral "4" at 537 corresponds to a healing abutment 500 with a diameter of 4 mm. It is contemplated in accordance with the present invention that other numerals could be placed on the top surface 529 of the healing abutment 500 to indicate other healing abutment diameters. Further, it is also contemplated that the numeral could represent the height of the healing abutment or the diameter of the underlying implant.

During the second stage of the prosthetic implementation process and after a healing abutment with the information markers has been placed, an impression of the mouth is made with only the healing abutments as described herein and without the use of an impression coping. A model of the impression is poured with, for example, die stone. Since the information markers are disposed on the top and/or side of the healing abutment, the laboratory has all necessary information to define the gingival aperture, the implant size and the orientation of the underlying hex. This enables the laboratory to quickly prepare the permanent components. The system of the present invention also allows the maintenance of the soft-tissue surrounding the healing abutment where in prior systems the soft tissue would close once the healing abutment was removed. The system spares the patient from the pain of removing the healing abutment.

Figure 8:
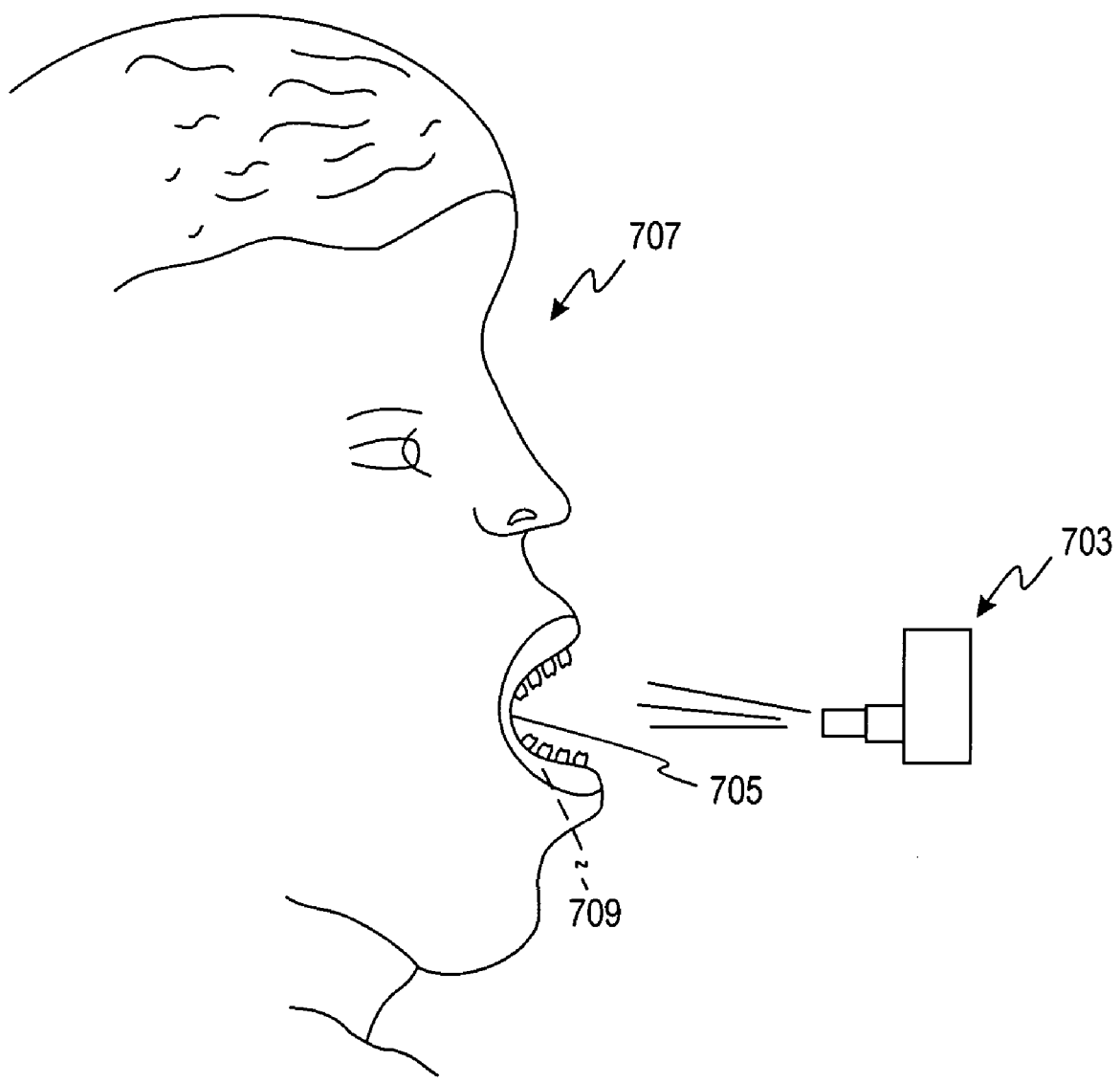
FIG. 8 is a side view of a method for stereophotographic imaging.

To create a permanent prosthesis, the dental region is scanned, as described above, from a stone model, from the impression material, or directly in the mouth using a laser scanning technique, a photographic scanning technique or a mechanical sensing technique. FIG. 8 shows stereophotographic imaging, one method used for scanning. Stereophotography with a camera 703 is performed directly on the mouth cavity 705 of the patient 707. A clinician can photograph implants and other components that have been placed into or adjacent the patient's jawbone 709.

The scanned information is then transferred into a graphical imaging program for analysis. The graphical imaging software program, due to the information markers on the surface of the healing abutment, can perform a wide variety of functions. The graphical imaging program can scan an opposing cast in order to develop an opposing occlusal scheme and relate this information back to the primary model. This feature is extremely important because many clinical patients have implants in both maxillary and mandibular locations.

The graphical imaging software program is capable of generating a three-dimensional image of the emergence profile contours used on the healing abutment. If the implant is not placed in the desired esthetic location, the software program relocates the position of the restoration emergence through the soft tissue. The graphical imaging software program is also able to accurately relate the gingival margin for all mold, model, implant and abutment dimensions. The software creates a transparent tooth outline for superimposition within the edentulous site. The occlusal outline of the "ghost" tooth should, if possible, be accurate and based on the scanned opposing occlusal dimensions. It is contemplated in accordance with the present invention that an occlusal outline is created by scanning a wax-up in order to maintain a proper plane of occlusion and healing abutment height.

The software program subtracts a given dimension from the mesial, distal, buccal, lingual, and occlusal areas of the superimposed tooth dimension. This allows for an even reduction of the healing abutment during fabrication to allow for proper thickness of the overlying materials (e.g., gold, porcelain, targis, etc.). The graphical imaging software program also incorporates angulation measurements into the custom abutment and subsequently calculates the dimensions of the prosthesis that are checked and modified, if necessary, by a laboratory technician. Each of the features is analyzed and determined from the different information markers that exist on the healing abutments of the present invention.

The final dimensional information determined by the graphical imaging computer program is transferred from the computer to a milling machine (e.g., a 5-axis milling machine) to fabricate the custom abutment. It is contemplated in accordance with the present invention that the custom abutment can be fashioned from gold or titanium or other similar metals or composites. A custom milled coping can then be fabricated. It is contemplated in accordance with the present invention that the custom milled coping can be formed from titanium, plastic, gold, ceramic, or other similar metals and composites.

FIG. 7 shows the exploded view of another embodiment of the present invention. A cap 602 is placed on a healing abutment 600 and later removed during the process of taking the impression of the healing implant and surrounding features of the patient's mouth. It is contemplated in accordance with the present invention that the cap 602 could be formed from plastic or metal or a composite material. As shown in FIG. 7, notches 604 are formed in the side(s) of the healing abutment 600. These notches correspond to notches 606 that have been preformed in the cap 602. When the cap 602 is placed onto the healing abutment 600, the cap only fits snugly and properly if the number of notches 606 in the cap 602 corresponds exactly to the number of notches 604 in the side wall(s) of the healing abutment. It is contemplated in accordance with the present invention that there could be many less or more notches than is depicted in FIG. 7. These notches correspond to information parameters such as healing abutment height, healing abutment and/or implant diameter and other parameters as listed above.

Specifically, after the healing abutment has been secured to the implant, the cap 602 is securely placed over the top of the healing abutment 600. The impression material is then placed over the top of the cap 602. The impression is then either scanned in the patient's mouth or the impression material (with the cap 602) is then scanned and the process continues as described above.

Figures 9A, 9B, 9C, 9D:
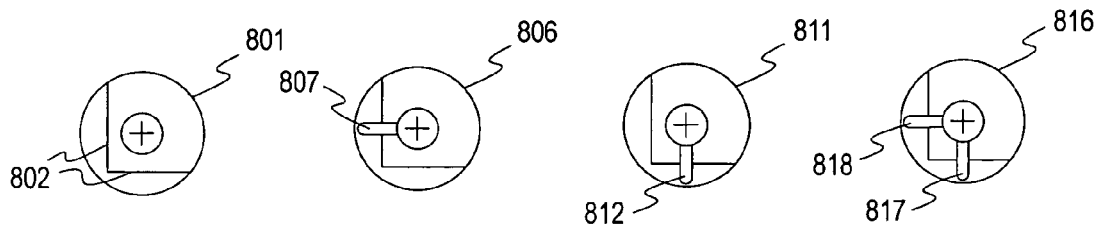
FIGS. 9a-9p are top views of a plurality of healing abutments having a binary-type system of information markers.
Figures 9E, 9F, 9G, 9H:
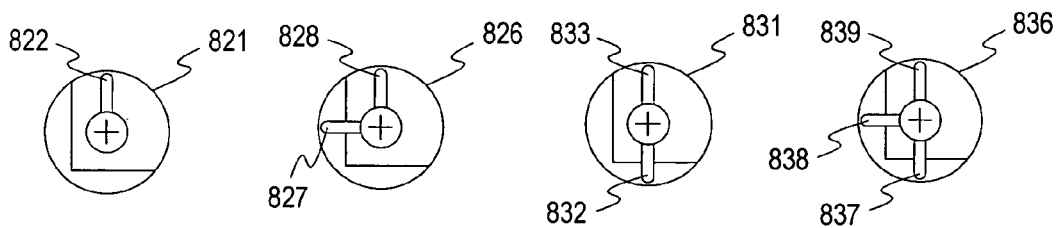
FIG. 9q is a top view of a healing abutment having a bar code information marker.
Figures 9I, 9J, 9K, 9L:
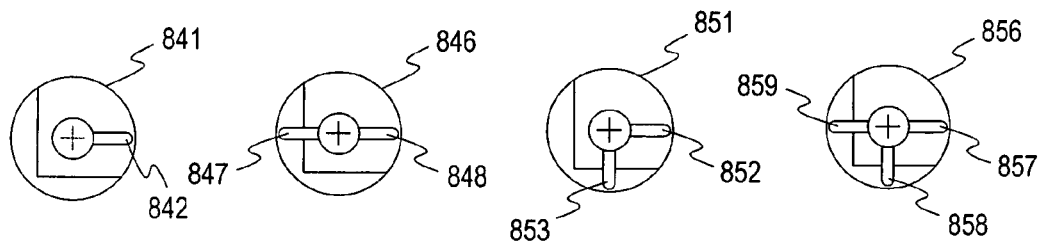
Figures 9M, 9N, 9O, 9P:
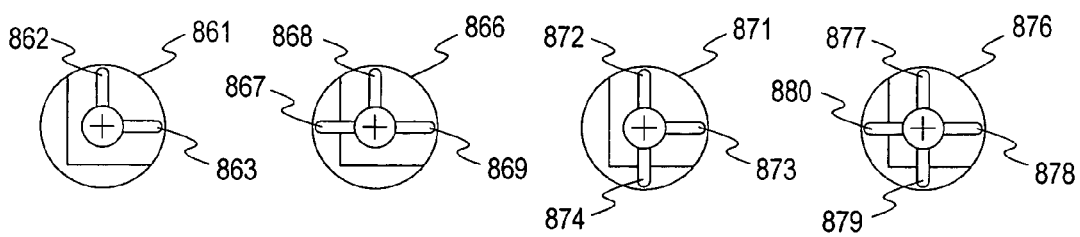

FIGS. 9a-9p depict yet another embodiment of the present invention. Specifically, FIGS. 9a-9p show the top view of a plurality of healing abutments, each of which has four marking locations on the top surface of the healing abutment. For each healing abutment, a marker is either present or absent in each of the four marking locations, and the presence or absence can be interpreted either visually or by a scanning device. As explained below in detail, the markers in the marking locations permit identification of healing abutment characteristics, such as dimensions of the healing abutment.

In FIGS. 9a-9p, the four rows correspond to four different healing abutment heights (e.g., 3 mm, 4 mm, 6 mm, and 8 mm). The four columns of the coding key correspond to four different diameters of the healing abutment seating surfaces (e.g., 3.4 mm, 4.1 mm, 5.0 mm, and 6.0 mm). Accordingly, sixteen unique healing abutments are present.

The top surface of each of the healing abutments has from zero to four information markers located in the four marking locations. As shown in FIGS. 9a-9p, the marking locations extend radially from a central region of the healing abutment to the outer region of the top surface of the healing abutments (i.e., at locations of 12 o'clock, 3 o'clock, 6 o'clock, and 9 o'clock).

As is well known, a binary-coded system exists as an array of digits, where the digits are either "1" or "0" that represent two states, respectively, ON and OFF. For each marking location, the presence of a marker ("ON") is a 1 and the absence of a marker ("OFF") is a 0. By grouping sets of 1's and 0's together, information about each healing abutment is known. In the illustrative embodiment, the determination of the sets of 1's and 0's derived from the information markers (e.g., via visual inspection, scanning in the mouth, scanning of the impression, or scanning of the model created by the impression) provide information on the height of the healing abutment and the diameter of the seating surface of the attached implant.

The information markers shown in FIGS. 9a-9p are in the form of grooves having rounded cross-sections. The present invention, however, provides that the cross-section of these grooves can be rectangular, triangular, or various other shapes. When an impression is created from the healing abutment, the grooved marking locations produce a protruding "mound"-like element in the impression. This impression is then scanned so that identifying features regarding the healing abutment can be obtained. Alternatively, a model of the patient's mouth is created from the impression such that the markings are again grooves in the model that substantially replicate the grooves in the healing abutments. Of course, the markers could also be protrusions instead of grooves. Further, if the unique characteristics of the healing abutment are to be identified through scanning in the mouth or simply visual scanning by the clinician, then markers not producing features in impression material, such as etched or laser marking, may also be used.

Turning now to the specifics of each healing abutment, FIG. 9a illustrates a top view of a healing abutment 801 that includes orientation pick-ups 802. These orientation pick-ups 802 are also present in each of the healing abutments shown in FIGS. 9b-9p. The most counterclockwise of the orientation pick-ups 802 (i.e., the horizontal pick-up at the lower region of FIGS. 9a-9p) is always parallel to one flat of the implant hex, as viewed from the top of the healing abutment. As shown, the orientation pick-ups 802 are a pair of bevels on the sides of the healing abutments in FIGS. 9a-9p. Alternatively, the orientation pick-ups 802 can be grooves or protruding ridges, as well.

The orientation pick-ups 802 serve a second function in that they dictate which of the four marking locations is the first marking location. The other three marking locations are then read in clockwise order, proceeding from the most counterclockwise pick-up 802 to the other three marking locations on the top surface of the healing abutment. In other words, as illustrated in FIGS. 9a-9p, the information marker at 6 o'clock is the first digit in the binary code, the information marker at 9 o'clock is the second digit in the binary code, the information marker at 12 o'clock is the third digit in the binary code, and the information marker at 3 o'clock is the fourth digit in the binary code. In summary, the position of the orientation pick-ups 802 allows for the determination of the position of one of the hex flats of the healing abutment (and, likewise, one of the hex flats on the implant), and also the starting point to check for the presence or absence of information markers.

The results of a scan (computer or visual) of the four information markers on the healing abutment 801 produce no information markers at the four marking locations on the healing abutment 801 of FIG. 9a. Thus, the binary code for the healing abutment 801 is 0000, indicating that no grooved marker is present in any of the four predetermined positions. Since the coding key is preset (on a chart or in computer software), the binary code 0000 indicates that the healing abutment 801 is a resident of first row and first column of the matrix depicted by FIG. 9, having a height of 3 mm and a seating surface diameter of 3.4 mm. Thus, the three distinct pieces of information obtained from the top of the healing abutment allow the clinician or laboratory to know (i) the orientation of the hex of the implant, (ii) the height of the healing abutment (i.e., the location of the implant's seating surface below the healing abutment), and (iii) the seating surface diameter of the healing abutment (or the size of the implant's seating surface).

The healing abutment 806 in FIG. 9*b* possesses a binary code of 0100because only one information marker 807 is present in the second marking location. Thus, it is understood from the binary code that the healing abutment 806 is 3 mm in height and has a seating surface diameter of 4.1 mm. The two healing abutments 811, 816 in FIGS. 9*c*, 9*d* have binary codes of 1000 and 1100, respectively. Healing abutment 811 has an information marker 812 in the first marking location, while healing abutment 816 has information markers 817, 818 in the first two locations. Thus, the unique characteristics of these two healing abutments are known.

The healing abutments 821, 826, 831, 836 shown in FIGS. 9*e*-9*h* and having heights of 4 mm, but with varying seating surface diameters, would be interpreted as having binary codes 0010, 0110, 1010, and 1110, respectively. Healing abutment 821 has one information marker 822 present in the third marking location, thus resulting in a binary code of 0010, which is indicative of a healing abutment height of 4 mm and a seating surface diameter of 3.4 mm. Similar analyses on healing abutment 826 with information markers 827, 828, healing abutment 831 with information markers 832, 833, and healing abutment 836 with information markers 837, 838, 839 allow determinations of the unique characteristics of these healing abutments.

The healing abutments 841, 846, 851, 856 shown in FIGS. 9*i*-9*l* and having heights of 6 mm, but with varying seating surface diameters, would be interpreted as having binary codes 0001, 0101, 1001, and 1101, respectively. Healing abutment 841 has one information marker 842 present in the fourth marking location, thus resulting in a binary code of 0001, which is indicative of a healing abutment height of 6 mm and a seating surface diameter of 3.4 mm. Similar analyses on healing abutment 846 with information markers 847, 848, healing abutment 851 with information markers 852, 853, and healing abutment 856 with information markers 857, 858, 859 allow determinations of the unique characteristics of these healing abutments.

The healing abutments 861, 866, 871, 876 shown in FIGS. 9*m*-9*p* and having heights of 8 mm, but with varying seating surface diameters, would be interpreted as having binary codes 0011, 0111, 1011, and 1111, respectively. Healing abutment 861 has two information markers 862, 863, which is indicative of a healing abutment height of 8 mm and a seating surface diameter of 3.4 mm. Similar analyses on healing abutment 866 with information markers 867, 868, 869, healing abutment 871 with information markers 872, 873, 874, and healing abutment 876 with information markers 877, 878, 879, 880 allow determinations of the unique characteristics of these healing abutments.

While the matrix of the sixteen healing abutments in FIGS. 9*a*-9*p* show four implant seating surface diameters and four heights, the matrix could include other physical characteristics of the healing abutment. For example, the maximum diameter of the healing abutment could be information obtainable through the binary-coded system. The type of fitting on the healing abutment and, thus, the implant (i.e., internal hex or external hex) could be provided. Information unrelated to the healing abutment, but related to only the implant, could be used. For example, the manufacturer of the implant could be noted. Or, information regarding the type of screw that mates with the internally thread bore of the implant could be provided.

Further, while FIGS. 9*a*-9*p* demonstrate the ability of the four digit, binary-coded system to provide two physical characteristics of the healing abutment, it could provide three or more physical characteristics. For example, two seating surface sizes, four heights, and two maximum diameters would provide sixteen unique healing abutments. If more information were needed, a fifth marking location could be added to provide the opportunity for displaying thirty-two physical characteristics of the healing abutments and/or implant. And, while one marking location has been shown with marker, it is possible to have two or more markers in each marking location. For example, one circumferential groove and one radial groove within one location could represent two digits of a binary system. Alternatively, having two widths possible for each groove could provide additional indicia representative of certain information about the healing abutment.

While the invention has been described with round healing abutments, healing abutments anatomically shaped like teeth can take advantage of the information markers. Thus, the set of healing abutments could include components shaped like the various teeth, and the information markers could provide the information regarding which tooth shape is present on the healing abutment. For example, a set may include four types of molar-shaped healing abutments, four types of bicuspid-shaped healing abutments, four types of incisor-shaped healing abutments and four types of round abutments. The four information marker locations on each component in the set provide the information to determine which one of the sixteen healing abutments is being used.

It is contemplated that the present invention also covers a set of eight unique healing abutments (as opposed to the sixteen shown) requiring only three marking locations. The computer software and/or the visual chart in this situation would identify these eight unique healing abutments through binary codes possessing three digits. The potential binary codes corresponding to an ON or OFF determination at the three marking locations are 000, 100, 010, 001, 110, 101, 011, and 111. Similarly, if the set has only four unique healing abutments, only two marking locations would be required on the healing abutments to determine features regarding the healing abutment and the attached dental implant. The potential binary codes in a four healing abutment matrix are 00, 10, 01, and 11.

After the top surface of a healing abutment (or the impression of the top surface, or the model of the impression of the top surface) is analyzed, the orientation of the hex is known from the location of the orientation pick-ups 802 and, via the binary code, the abutment height and the seating surface of the healing abutment is known. Other information regarding the healing abutment and the attached implant can also be determined by adding other markers of the type previously shown.

Figure 9Q:
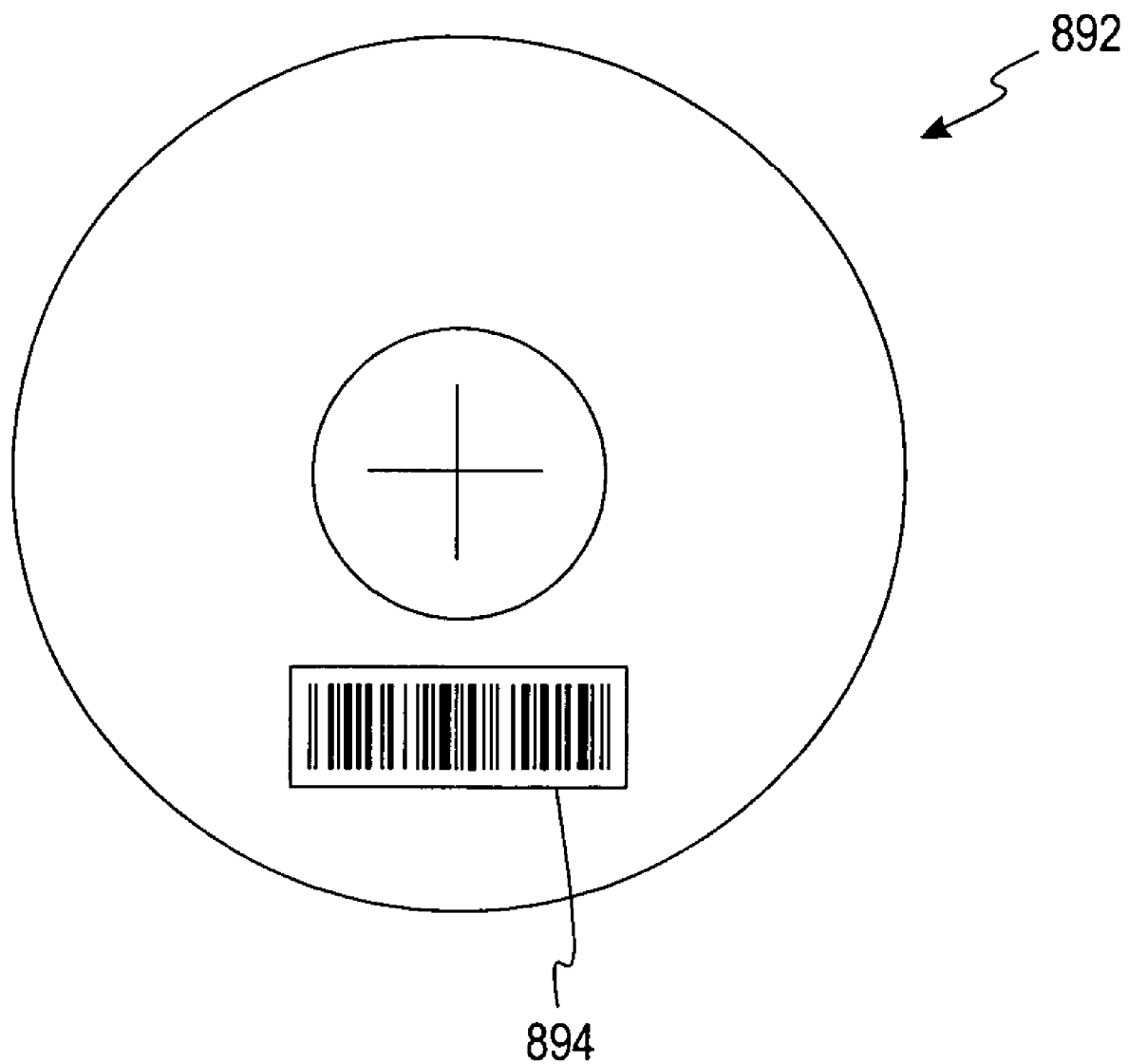

In addition to the markers described, it is further possible to provide a bar-coded system for providing information about the particular component, as shown in FIG. 9*q*. The bar code 894 can be located on the top surface on the healing abutment 892 such that it can be scanned or read easily. Thus, the bar code 894 would provide the same type of information described above with respect to the information markers.

Figure 10:
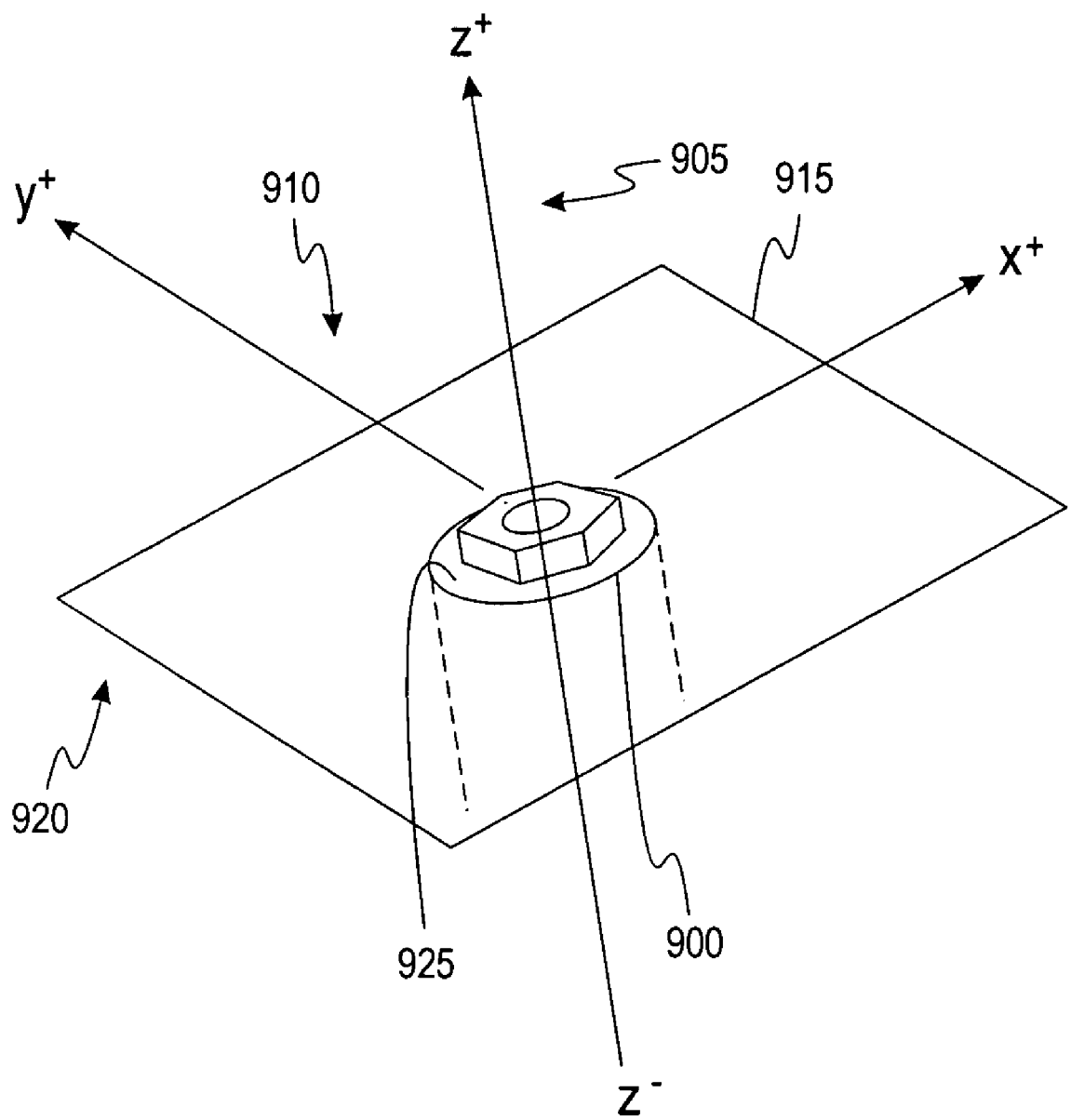
FIG. 10 is a perspective view of a coordinate system of one embodiment of the present invention.

Referring to FIG. 10, when scanning techniques are used to learn of the information on the top of the healing abutment, the computer software is able to determine the position and orientation of the implant 900 relative to the adjacent teeth. The position of the implant 900 is defined in a Cartesian coordinate system having "X," "Y," and "Z" axes. The common point is at the intersection of the centerline of the implant and a plane 920 representing the seating surface 925 of the implant 900.

As noted above, the information markers assist in determining the height of the healing abutment above the implant. This height can be used to identify the zero point on the "Z" axis, which is in the plane 920 containing the seating surface 925 of the implant 900. The "Y" axis 910 is within the plane 920 representing the seating surface 925 with the positive "Y" direction as close to the direction of facial to buccal as possible. The "X" axis 915 is in the plane 920 and is perpendicular to an implant hex face. Thus, the width of the seating surface 925 in the plane 920 is known, as is the width of the healing abutment emerging through the gingiva. Thus, the emergence profile of the artificial tooth is known, as well.

Figure 11:
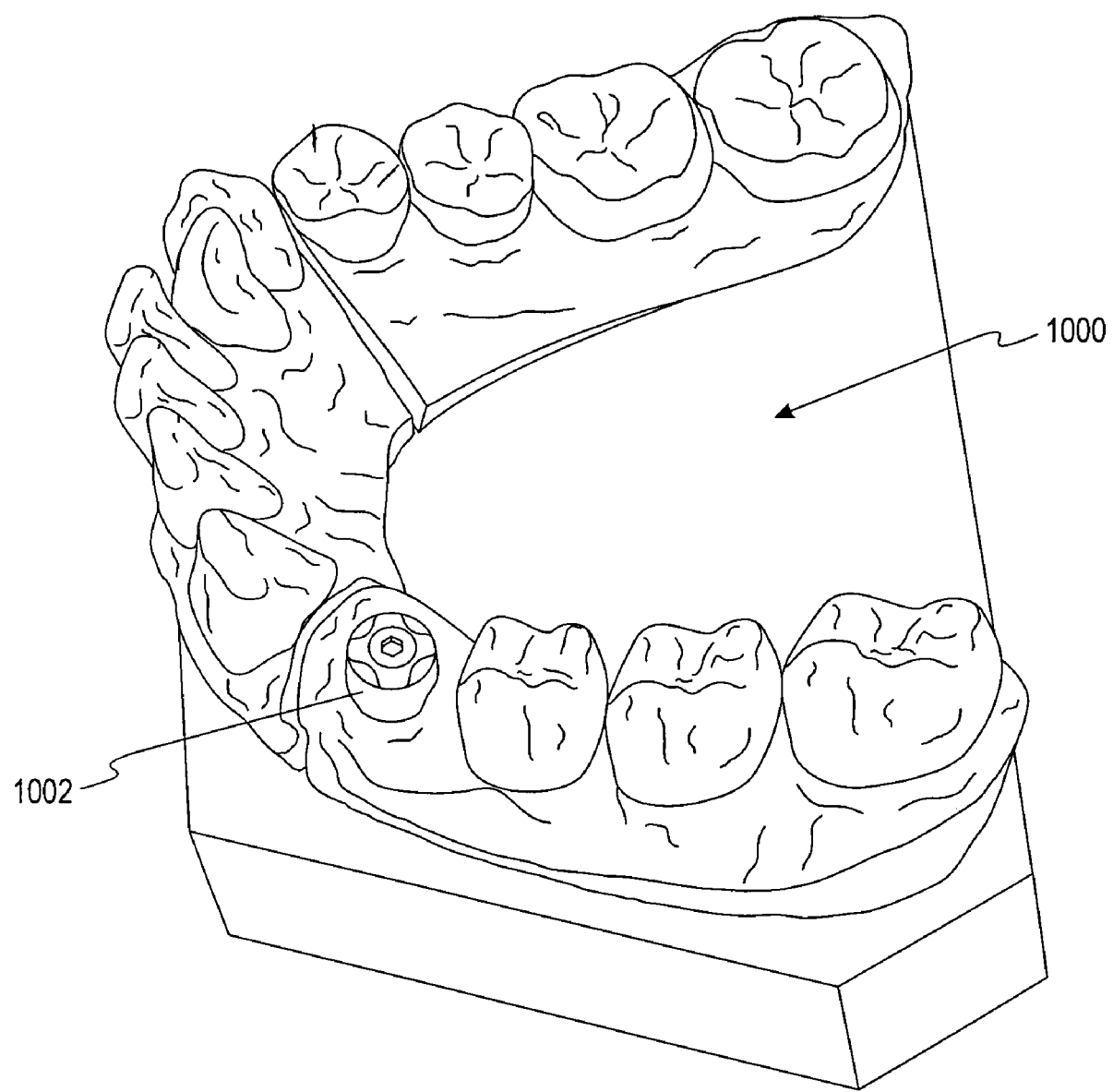
FIG. 11 is a perspective view of a stone model of an impression of a mouth used with one embodiment of the present invention.

Turning now to FIG. 11, a perspective view of a stone cast 1000 of a mouth of a patient is shown with a stone-cast model of a healing abutments 1002 which has configurations on its upper surface that corresponds to the healing abutments previously described. The stone cast 1000 is made from an impression of the mouth as previously described.

Figure 12:
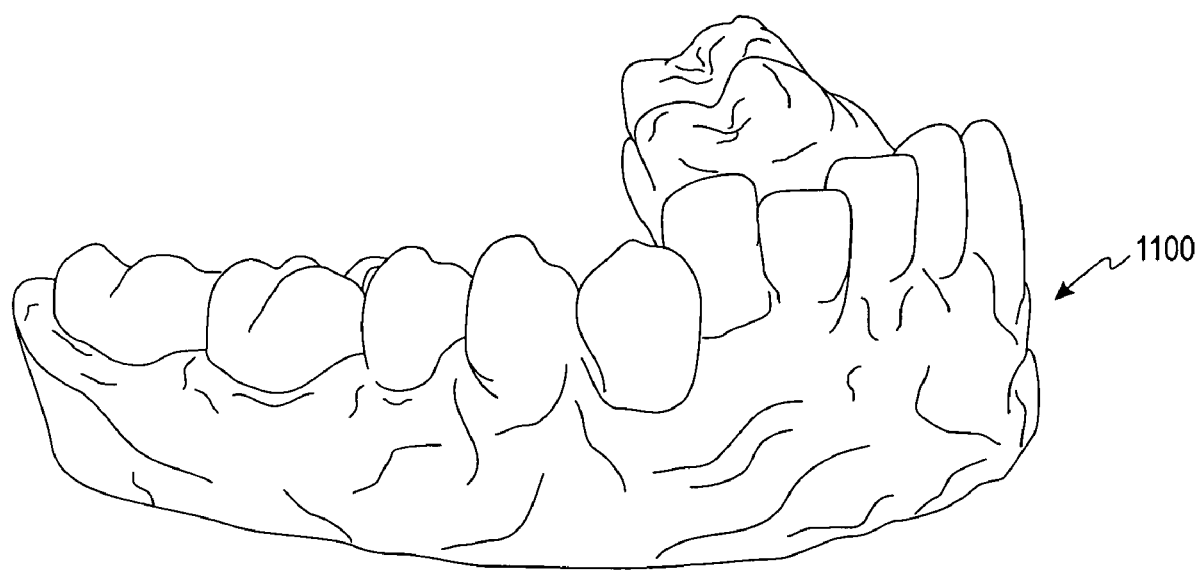
FIG. 12 is a perspective view of a 3-D CAD model of the stone model of FIG. 11.

Once the stone cast 1000 is prepared, it is scanned using a scanning technique previously described, the scanned data is transferred into a graphical imaging program, such as a Computer Aided Design ("CAD") program so that a three-dimensional ("3-D") CAD model 1100 of the stone cast 1000 (FIG. 11) is created, as shown in FIG. 12.

Figure 13:
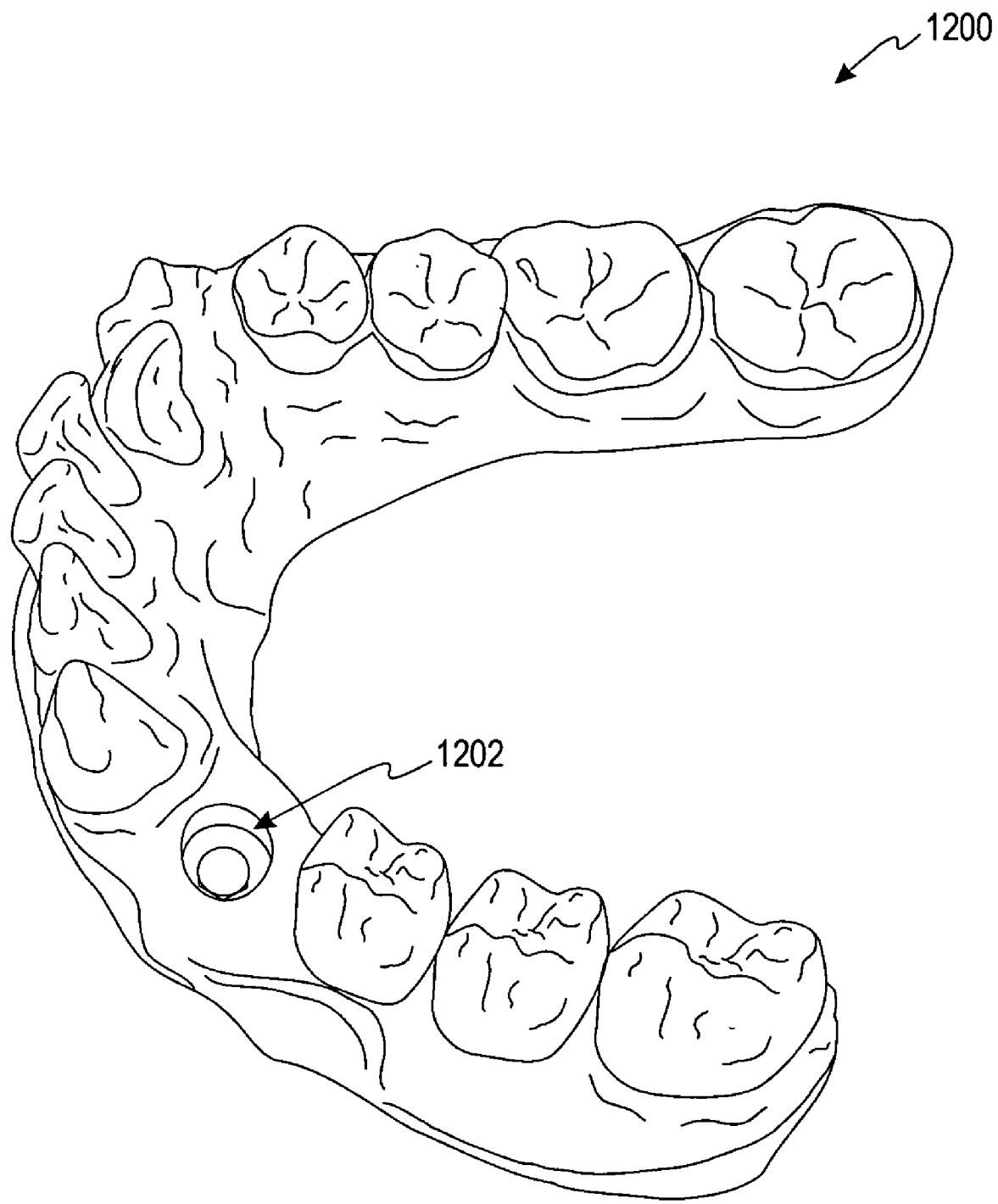
FIG. 13 is a perspective view of an altered 3-D CAD model of FIG. 12 with the healing abutments removed from the CAD model.

As shown in FIG. 13, the CAD model 1100 (FIG. 12) of the stone cast 1000 (FIG. 11) is modified to create a first modified CAD model 1200 that removes the healing abutment 1002 (FIG. 11) so that the position of an implant 1202, or the top surface of an implant, underlying the healing abutment 1002 (FIG. 11) is displayed.

The CAD program is additionally used to design a custom, patient specific, abutment adapted to attach to the implant 1202. The custom abutment supports a final prosthesis, often referred to as a crown. A modified version of the stone model 1000 is used to design the crown to fit between the adjacent teeth based on the specific dimensions and conditions of a patient's mouth. Thus, obtaining an accurate position of the dental implant is critical to designing an accurate crown. Once the CAD program has been used to sign a custom abutment, the design of the custom abutment is input into a precision manufacturing device, such as a CNC milling machine, to create the custom abutment from a blank of metal, usually titanium, or a titanium alloy, or from a ceramic material.

Figure 14:
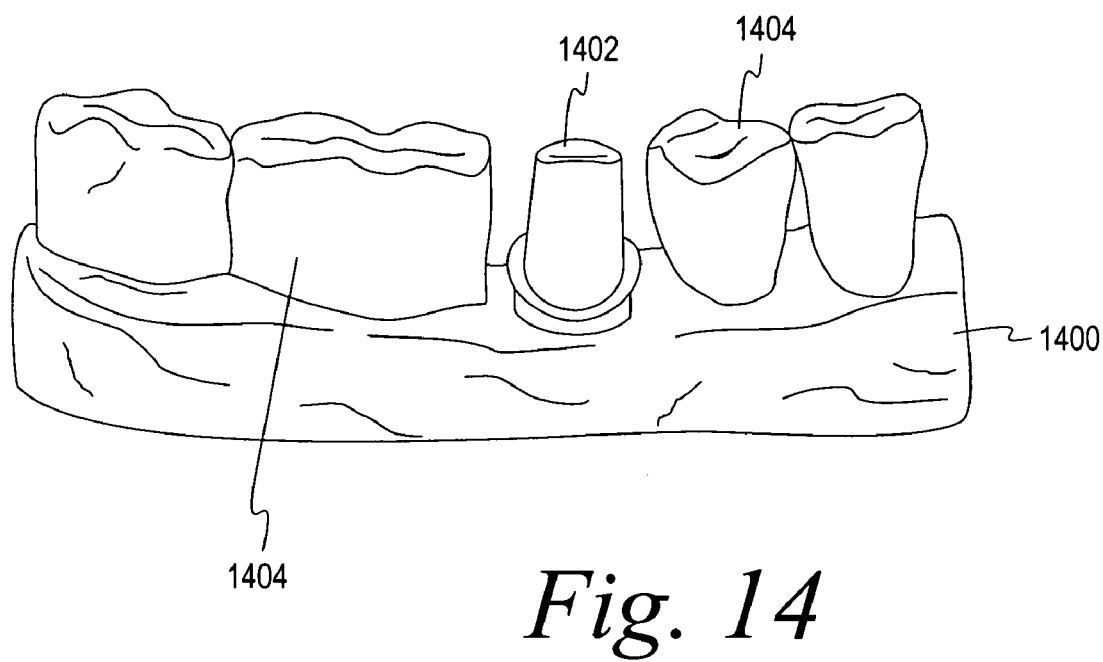
FIG. 14 is a perspective view of an altered 3-D CAD model of FIG. 13 with a custom abutment added in the CAD model.
Figure 15:
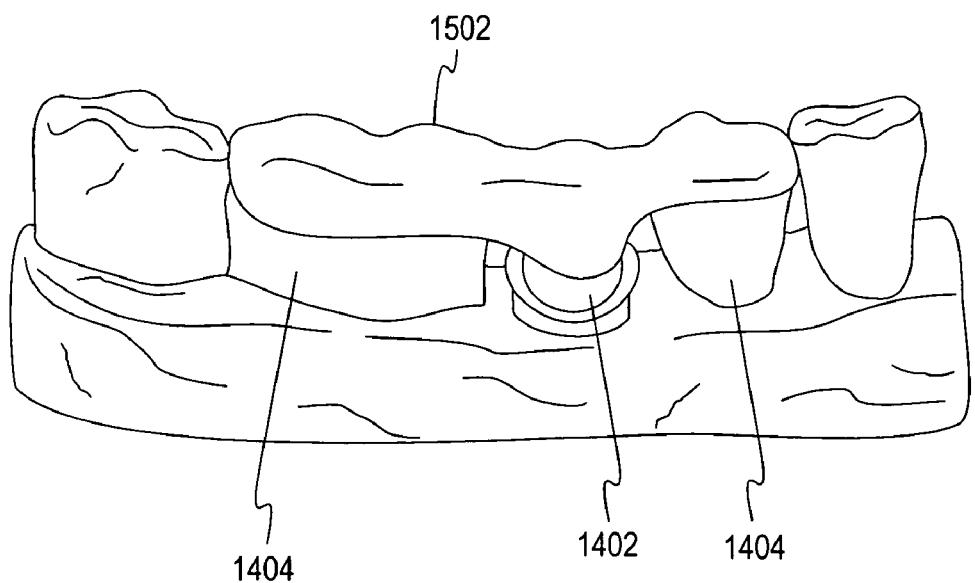
FIG. 15 is a perspective view of a 3-D CAD model with an overmold attached over the custom abutment and the adjoining teeth.

As shown in FIG. 14, a CAD model of a custom abutment 1402 is shown located between a CAD model of the adjacent teeth 1404 that has been created by scanning the stone model 1000. Using the CAD program, an overmold 1502 is created, as shown in FIG. 15. The overmold 1502 fits over the custom abutment 1402 and the adjacent teeth 1404 in the 3-D CAD model 1400. The overmold 1502 is adapted to fit over a stone model of the patient's teeth to allow an actual custom abutment 1604 (FIG. 18) to be positioned in substantially the identical location and orientation as the custom abutment 1402 in the 3-D CAD model 1400.

Once the overmold 1502 has been designed in the 3-D CAD model 1400, the CAD program allows a rapid prototype overmold 1602 (FIG. 16) corresponding to the 3-D CAD model of the overmold 1502 to be created using rapid prototype equipment. It is contemplated that many rapid prototyping techniques may be utilized with the present invention such as: stereolithography, laminated-object manufacturing, selective laser sintering, solid ground curing, or other known rapid prototyping processes. The 3-D CAD model of the overmold 1502 is used by the equipment controlling the rapid prototype equipment to create the rapid prototype overmold 1602.

Figure 16:
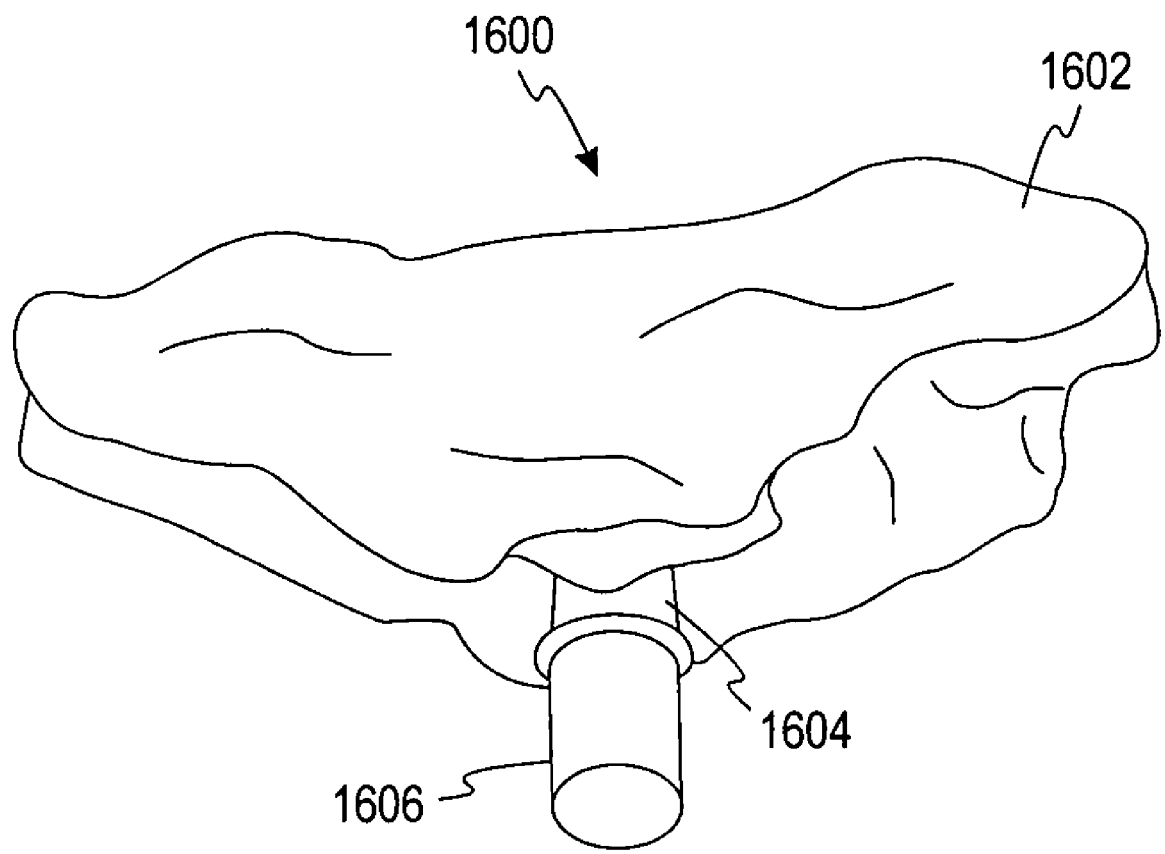
FIG. 16 is a perspective view of a rapid prototype of the overmold shown in the 3-D CAD model of FIG. 15 including an implant analog and an abutment.

Turning now to FIG. 16, a rapid prototype assembly 1600 is shown having the rapid prototype overmold 1602, a custom abutment 1604, and an implant analog 1606. The rapid prototype overmold 1602 is adapted to receive the custom abutment 1604 via a snap-fit connection created by snapping the overmold 1602 over an edge of the custom abutment 1604. It is additionally contemplated that a press fit may be used to secure a custom abutment to a rapid prototype overmold by using an interference fit. The custom abutment 1604 is secured to the implant analog 1606 using a screw.

Figure 17:
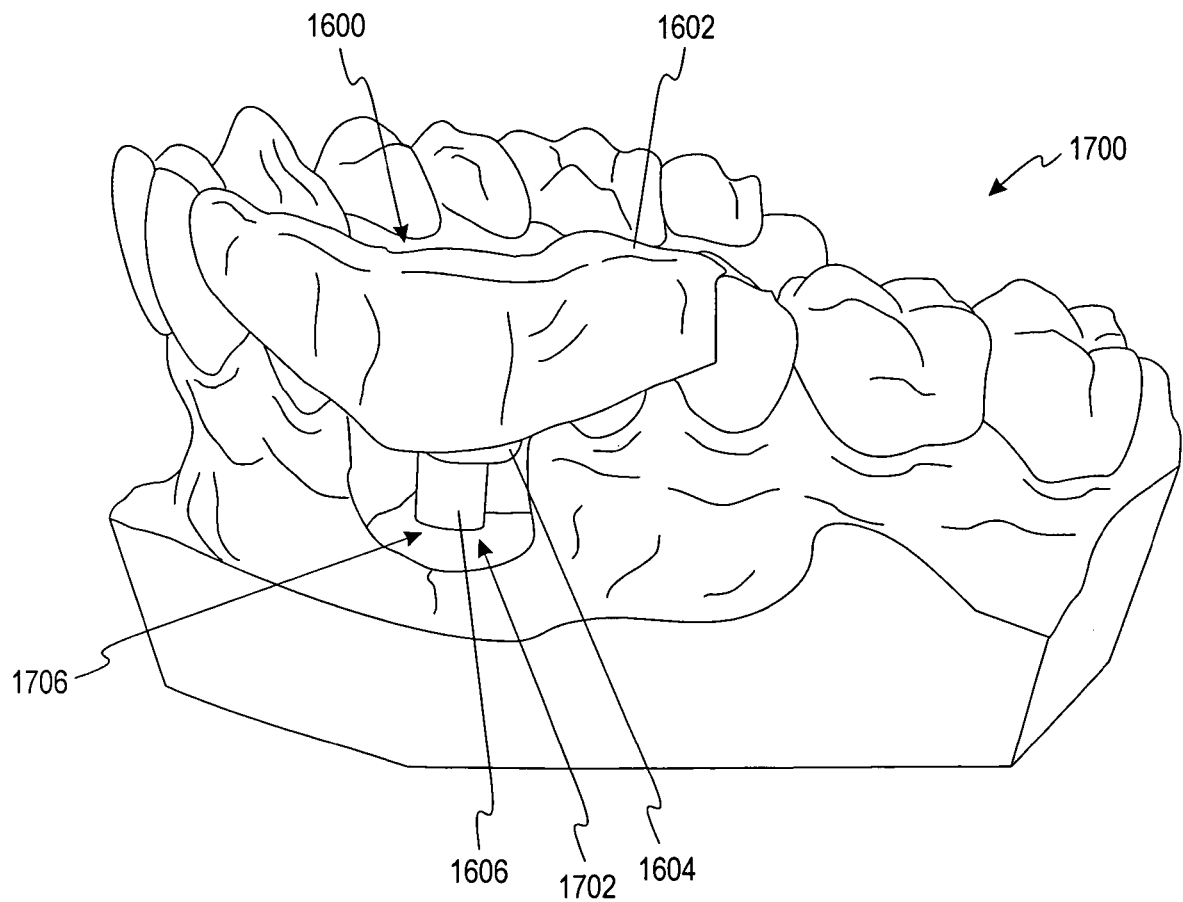
FIG. 17 is a perspective view of an altered stone model of FIG. 11 with the overmold of FIG. 16 attached.
Figure 18:
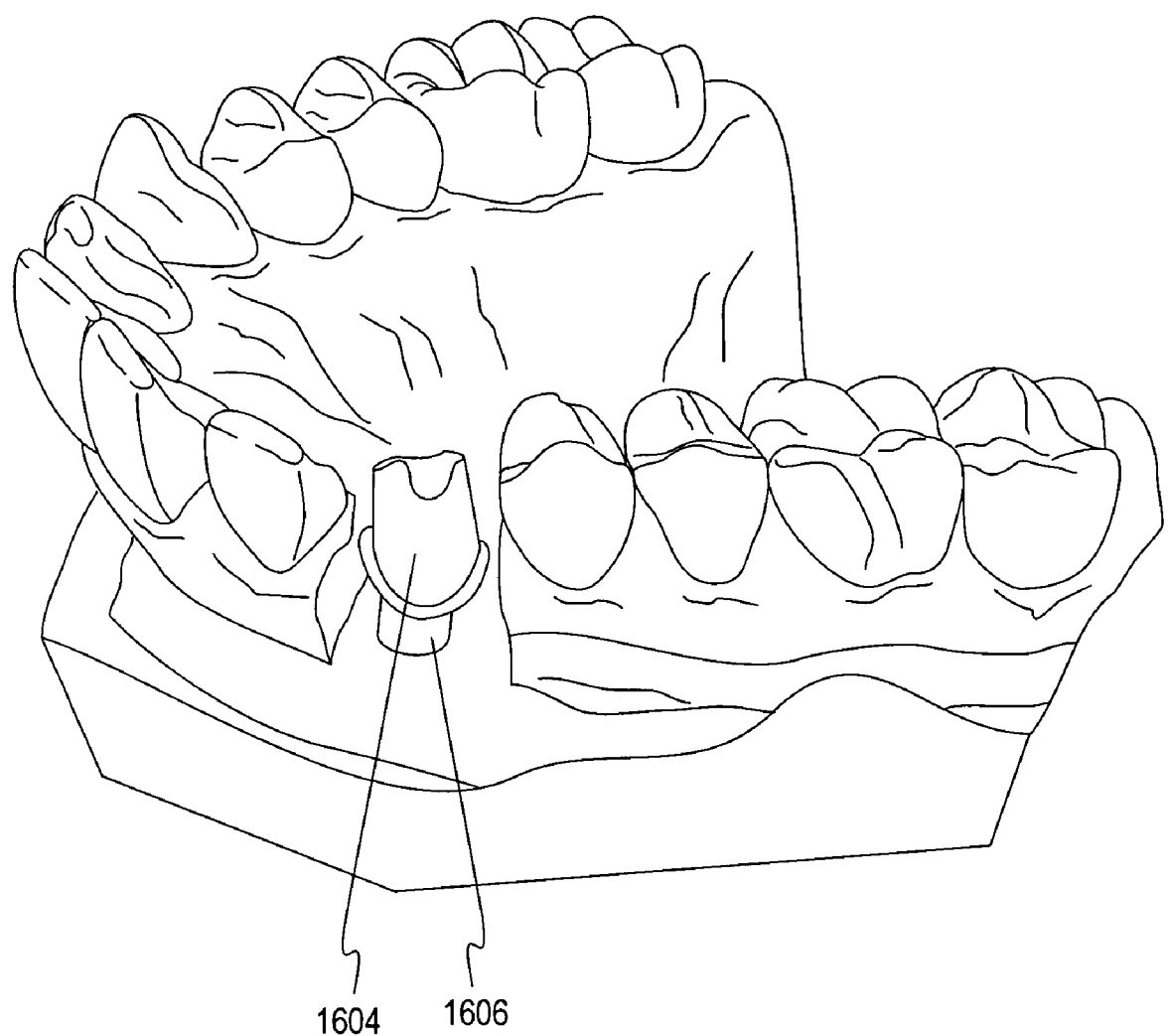
FIG. 18 is a perspective view of the altered stone model of FIG. 17 with the overmold removed and the implant analog placed in the stone model and the patient-specific abutment connected to the implant analog.

The custom abutment 1604 (FIG. 18) produced on the precision manufacturing device must then be placed within an altered stone model 1700 as shown in FIG. 17, so that the crown may be created. The altered stone model 1700 has had the healing abutment 1002 from the stone cast 1000 (FIG. 11) removed, so that an opening 1702 is present where the healing abutment 1002 from the stone cast 1000 (FIG. 11) had been located. The opening 1702 is of a sufficient size so as to receive the implant analog 1606. A gap 1706, or a hole large enough to receive an implant analog, exists in the stone model 1700 between the implant analog 1606 and the walls defining the opening 1702. The rapid prototype assembly 1600 is placed over the stone model 1700, positioning the custom abutment 1604 and the implant analog 1606 as in the 3-D CAD model. The gap 1706 is then filled with a securing material, such as epoxy, to secure the implant analog 1606 to the stone model 1700. Once the securing material sets, the implant analog 1606 is properly positioned within the stone model 1700, at substantially the same location as the implant in the patient's mouth relative to the teeth adjacent to the implantation site. The implant analog 1606 and the custom abutment 1604 may be removed from the rapid prototype overmold 1602, as shown in FIG. 18. The final prosthesis may then be created using the stone model 1700 having the properly positioned implant analog 1606 and custom abutment 1604.

Thus according to the present invention, the same stone model may be used for a scanning process to make the patient specific custom abutment 1604 and for receiving an implant analog 1606 for mating with the custom abutment 1604 to develop a final prosthesis.

While the preceding embodiment has been described for creating a final prosthesis, it is contemplated that the process may be used to create a temporary prosthesis as well.

According to anther embodiment of the present invention, an implant analog is placed within a stone model using a robot manipulator. As previously described herein, a stone cast 1000 of a mouth of a patient is produced from taking an impression of the patient's, mouth. The stone cast is scanned to generate a 3-D CAD model 1100 of the stone cast 1000. The CAD program is used to design a custom abutment 1604. The custom abutment 1604 is produced on a precision manufacturing device using information from the CAD program.

Figure 19A:
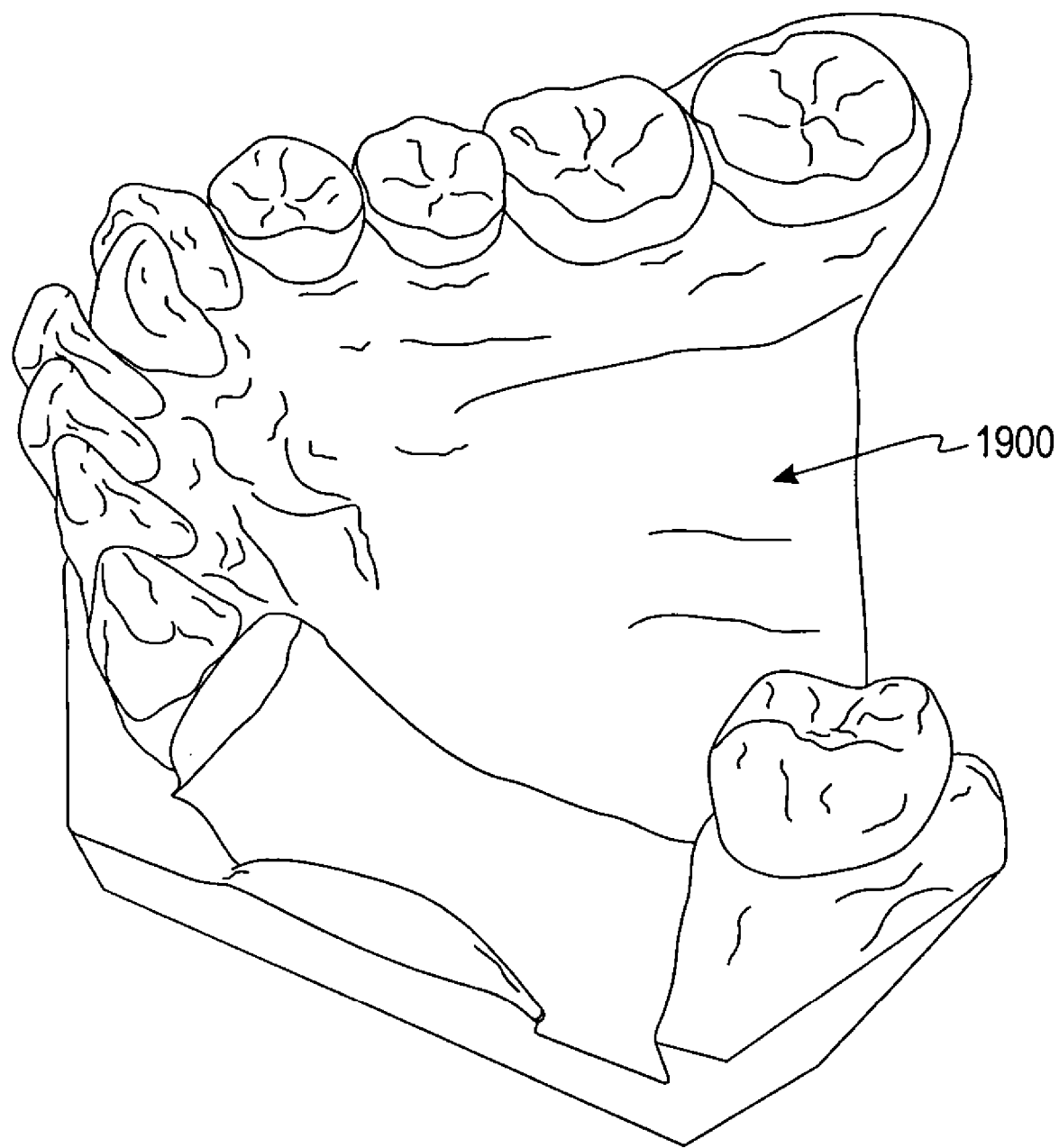
FIG. 19a is a perspective view of an embodiment of an altered stone model of a mouth with abutments removed.
Figure 20:
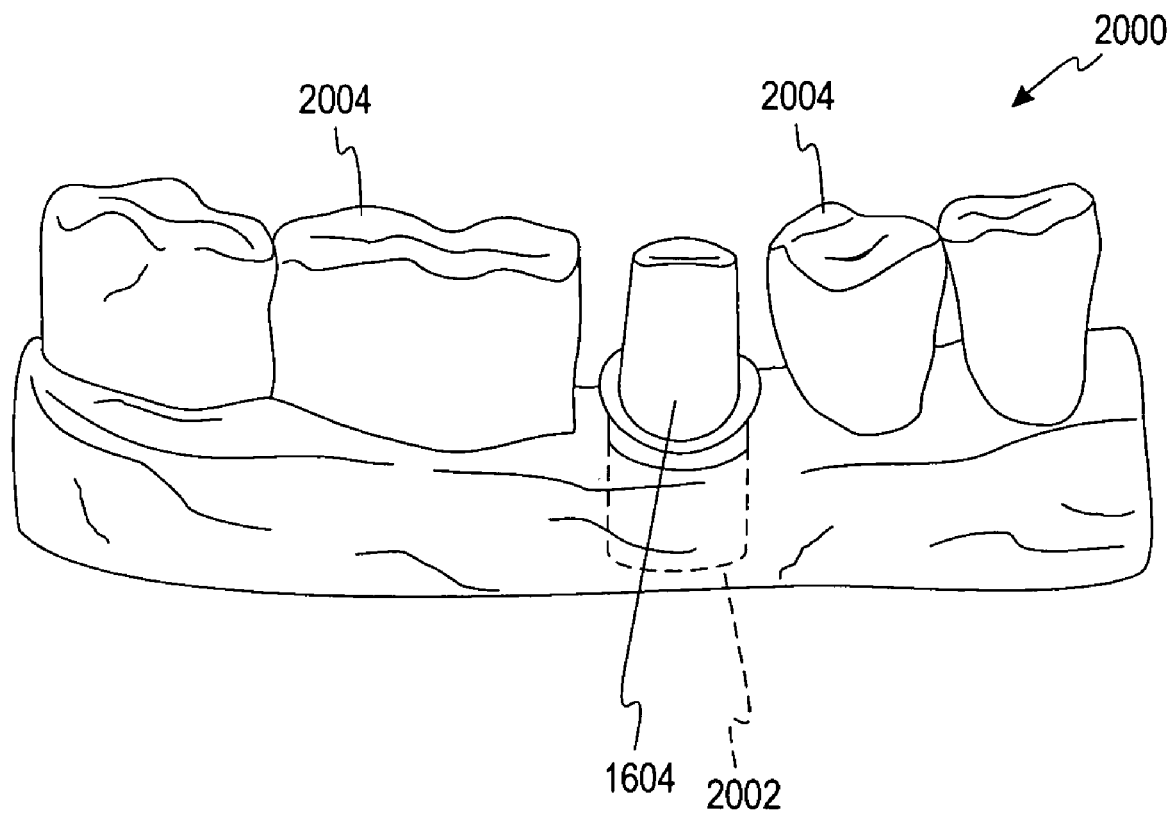
FIG. 20 is a perspective view of a 3-D CAD model of a custom abutment and implant analog placed within a mouth.
Figure 21:
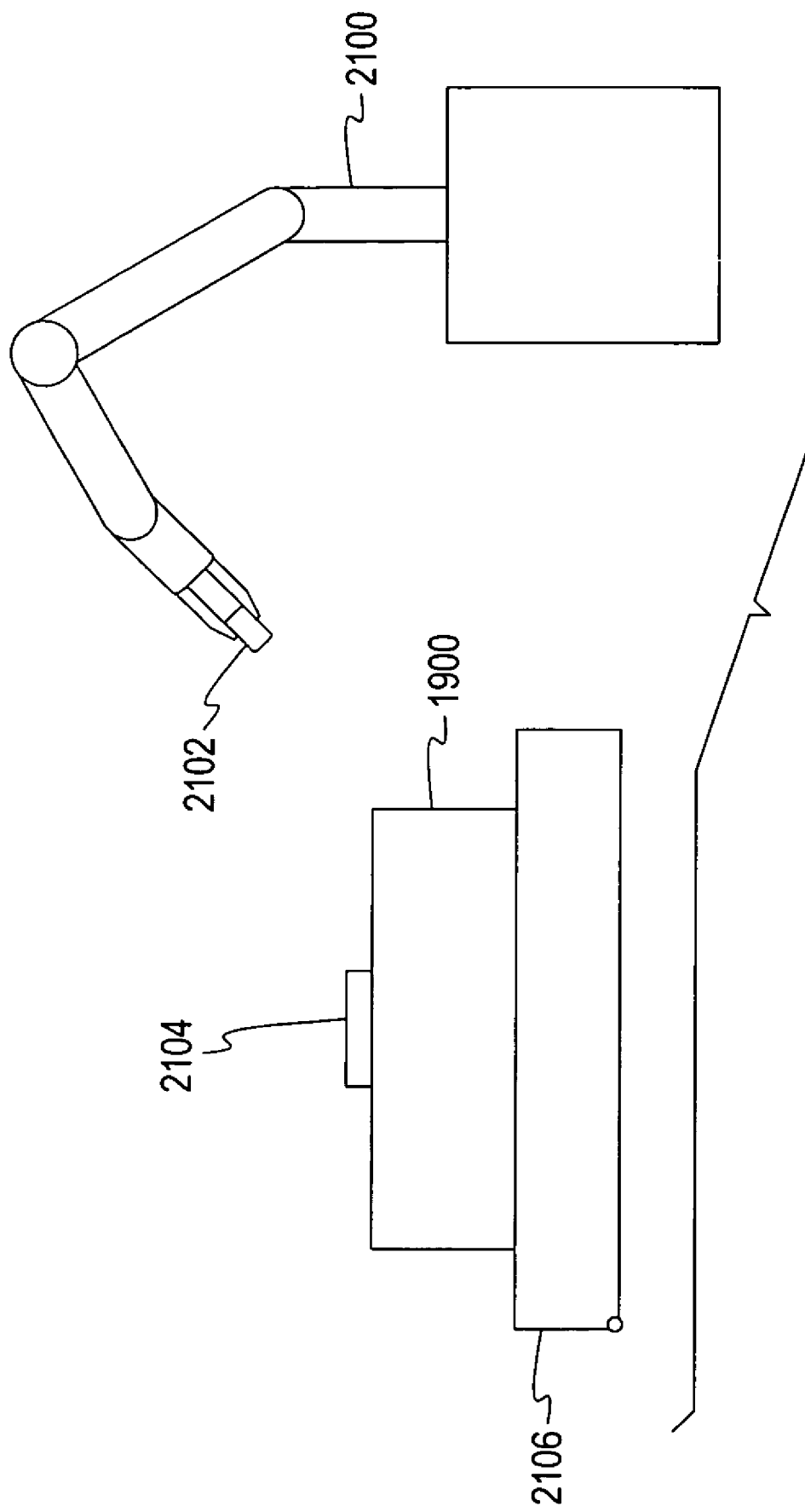
FIG. 21 is a schematic representation of a robot manipulator system adapted to place an implant analog into a stone model according to another embodiment of the present invention.

As shown in FIG. 19a, a modified stone cast 1900 is created by removing a section of the stone cast 1000 that contains the healing abutment 1002 (FIG. 11). The CAD program used to generate the custom abutment 1604 is used to generate a 3-D CAD model containing a custom abutment having an implant analog attached. Thus, a 3-D CAD model 2000 exists where the proper position of the implant analog 2002 relative to adjacent teeth 2004 is created as shown in FIG. 20. Using a coordinate system within the 3-D CAD model 2000, the relative position of the implant analogs 2002 and the adjacent teeth 2004 may be generated. A common base plate 2106 (FIG. 21) may be used in scanning the stone cast 1000 and in placing an implant analog 2102 (FIG. 21) using a robot manipulator 2100 (FIG. 21). The robot manipulator 2100 (FIG. 21) is located at a known position relative to the ase plate 2106 (FIG. 21). A scanner measures an X, Y, and Z position of the healing abutment 1002 in the stone cast 1000 relative to axes on the base plate 2106, also referred to as the base plate 2106 origin. Thus, when the base plate 2106 is in a known position with respect to the robot manipulator 2100, an exact location of an implant analog 2102 (FIG. 21) may be determined.

Once the relative position of the implant analog 2002 and the adjacent teeth 2004 has been generated, this position information is input to a robot manipulator. The robot manipulator 2100 uses the relative position information to place an implant analog 2102 into a securing material 2104, such as epoxy, located on the modified stone cast 1900 where the healing abutments had been located, as shown schematically in FIG. 21. The robot manipulator 2100 is able to accurately place the implant analog 2102 in the securing material 2104, such that the position of the implant analog 2102 within the modified stone cast 1900 is substantially identical to the position of the implant analog 2002 within the 3-D CAD model 2000.

Figure 19B:
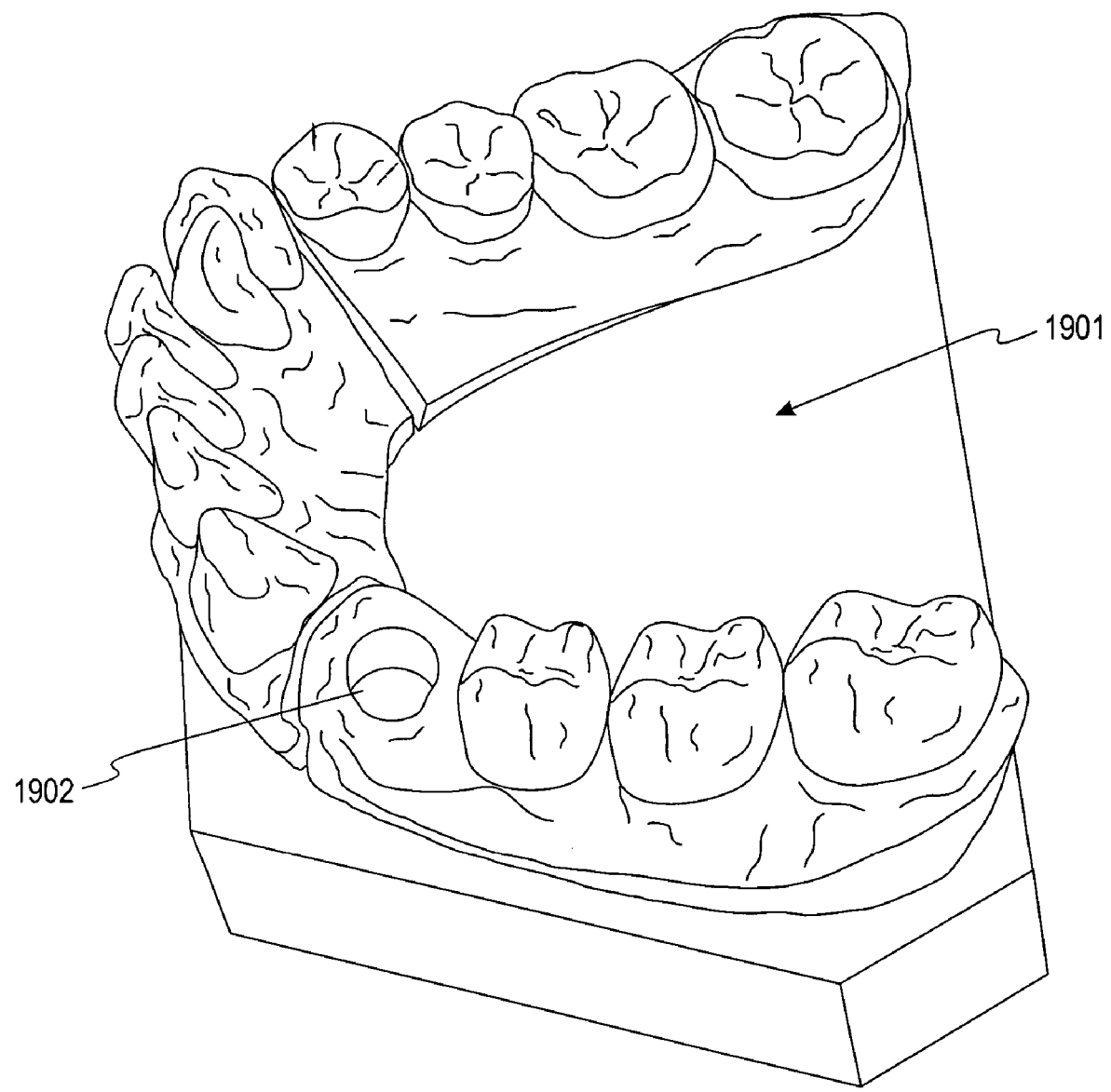
FIG. 19b is a perspective view of an alternative embodiment of an altered stone model of a mouth with abutments removed.

According to a further alternative embodiment of the present invention, instead of using a robot manipulator to place an implant analog into a securing material of a modified stone cast, the robot manipulator may instead be a multiple handed robot manipulator adapted to drill a hole 1902 in a stone cast 1901 (as shown in FIG. 19*b*) with a first hand, and place an implant analog in the hole with a second hand.

While the preceding embodiments have been described for creating a final prosthesis, it is contemplated that the process may be used to create a temporary prosthesis as well.

While the preceding embodiments have been described by scanning a cast of a patient's mouth, it is also contemplated that an intra-oral scan, a CT scan, or other known type of medical scan, may be taken to generate data used for a 3-D CAD model.

While the preceding embodiments have been described using a healing abutment containing a variety of markings, it is further contemplated that a scanning abutment may be placed into a stone model before a scan is performed. According to such an embodiment, a first stone model of a patient's mouth would be made, and a portion of the first stone model corresponding to a healing abutment would be removed and replaced with a scanning abutment containing a variety of markings as previously described. A scan would then be performed of the first stone model containing the scanning abutment, and a 3-D CAD model of the patient's mouth would be created. The 3-D CAD model would then be used as previously described.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of positioning an implant analog in a modified stone model of a patient's dentition for use in creating a patient specific prosthesis, comprising:
   preparing a stone model of a patient's dentition including teeth models and informational
      markers indicative of information concerning a dental implant installed in the patient's mouth;
   scanning the stone model;
   generating scan data from the scanning of the stone model;
   transferring the scan data to a CAD program;
   creating a three-dimensional model of at least a portion of the stone model on the CAD program using the scan data;
   determining the informational markers to gather information for manufacturing an abutment;
   developing abutment dimensional information based on the three-dimensional model and the information from the informational markers;
   developing implant analog positional information on the CAD program based on the information from the informational markers;
   transferring the implant analog positional information to a robot manipulator;
   modifying the stone model by removing a portion of the stone model in the region of the informational markers; and
   placing the implant analog on the modified stone model using the robot manipulator and the implant analog positional information.

2. The method of claim 1, wherein the scanning is one of a laser scanning technique, mechanical scanning technique, photographic scanning technique, and stereophotographic imaging technique.

3. The method of claim 1, further including manufacturing an abutment from the abutment dimensional information.

4. The method of claim 1, further including developing the patient specific prosthesis using the abutment and the modified stone model.

5. The method of claim 1, wherein the modifying the stone model includes using the robot manipulator to develop a bore in the model for receiving the implant analog.

6. A method of positioning an implant analog in a modified stone model of a patient's dentition, comprising the acts of:
   creating, on a CAD program, a three-dimensional computer model of a stone model of a patient's mouth that includes an implant installation site, the stone model including features at the implant installation site for indicating the location of an underlying dental implant;
   determining, with the use of the features, the location and orientation of a dental implant within the implant installation site;
   generating implant analog positional information with respect to the stone model on the CAD program;
   transferring the implant analog positional information to a robot manipulator;
   modifying the stone model by removing a portion of the stone model in the region of the stone model corresponding to the implant installation site; and
   placing the implant analog on the modified stone model using the robot manipulator and the implant analog positional information.

7. The method of claim 6, further including developing, on a CAD program, a three-dimensional image of an abutment for mating with the dental implant, the abutment for mating with the implant analog for developing a patient specific prosthesis.

8. The method of claim 6, wherein the modifying the stone model includes using the robot manipulator to develop a bore in the model for receiving the implant analog.

9. The method of claim 6, wherein the features are derived from informational markers on a healing abutment that is mounted to the implant.

* * * * *

UNITED STATES PATENT AND TRADEMARK OFFICE
CERTIFICATE OF CORRECTION

PATENT NO. : 7,661,956 B2 Page 1 of 1
APPLICATION NO. : 11/585705
DATED : February 16, 2010
INVENTOR(S) : Powell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this

Thirtieth Day of November, 2010

David J. Kappos
*Director of the United States Patent and Trademark Office*